United States Patent
Srinivasan et al.

(10) Patent No.: US 11,236,050 B2
(45) Date of Patent: Feb. 1, 2022

(54) POLYMORPHS OF 4-[3-CHLORO-4-(N'-CYCLOPROPYL UREIDO)PHENOXY]-7-METHOXYQUINOLINE-6-CARBOXAMIDE, ITS SALTS AND PROCESS FOR THE PREPARATION THEREOF

(71) Applicants: MSN LABORATORIES PRIVATE LIMITED, R&D CENTER, Telangana (IN); Thirumalai Rajan Srinivasan, Hyderabad (IN)

(72) Inventors: Thirumalai Rajan Srinivasan, Hyderabad (IN); Eswaraiah Sajja, Hyderabad (IN); Venkata Panakala Rao Gogulapati, Hyderabad (IN); Rajeshwar Reddy Sagyam, Hyderabad (IN); Pavan Kumar Reddy Bandla, Hyderabad (IN); Srinivasulu Rangineni, Hyderabad (IN)

(73) Assignee: MSN LABORATORIES PRIVATE LIMITED, R&D CENTER, Telangana (IN)

( * ) Notice: Subject to any disclaimer, the term of this patent is extended or adjusted under 35 U.S.C. 154(b) by 0 days.

(21) Appl. No.: 16/771,096

(22) PCT Filed: Dec. 8, 2018

(86) PCT No.: PCT/IN2018/050823
§ 371 (c)(1),
(2) Date: Jun. 9, 2020

(87) PCT Pub. No.: WO2019/111283
PCT Pub. Date: Jun. 13, 2019

(65) Prior Publication Data
US 2021/0188778 A1 Jun. 24, 2021

(30) Foreign Application Priority Data

Dec. 9, 2017 (IN) .............................. 201741044293
Mar. 2, 2018 (IN) .............................. 201841007887
Jun. 2, 2018 (IN) .............................. 201841020743

(51) Int. Cl.
C07D 215/18 (2006.01)
C07D 215/48 (2006.01)

(52) U.S. Cl.
CPC ........ *C07D 215/48* (2013.01); *C07B 2200/13* (2013.01)

(58) Field of Classification Search
CPC .......................... C07D 215/18; C07B 2200/13
See application file for complete search history.

(56) References Cited

U.S. PATENT DOCUMENTS

2007/0004773 A1 4/2007 Sakaguchi et al.
2018/0155291 A1* 6/2018 Chen ....................... A61P 35/00

FOREIGN PATENT DOCUMENTS

| WO | WO 2004101526 | 11/2001 |
| WO | WO 2005063713 | 7/2007 |
| WO | WO 2016/184436 | 11/2016 |

* cited by examiner

Primary Examiner — Timothy R Rozof
(74) Attorney, Agent, or Firm — IP Pundit LLC

(57) ABSTRACT

The present invention relates to novel polymorphs of 4-[3-chloro-4-(N'-cyclopropyl ureido) phenoxy]-7-methoxyquinoline-6-carboxamide methanesulfonate represented by following structural formula-1a and process for preparation thereof.

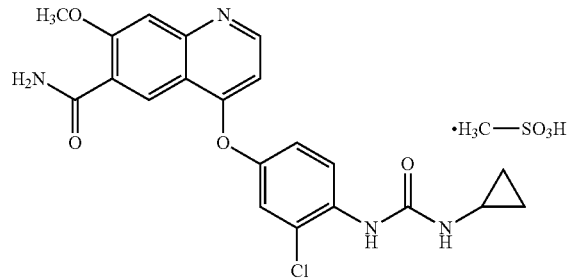

Formula-1a

Further, the present invention relates to an improved process for the preparation of 4-[3-chloro-4-(N'-cyclopropylureido) phenoxy]-7-methoxyquinoline-6-carboxamide compound of formula-1 or its salts and its intermediates thereof.

12 Claims, 12 Drawing Sheets

POLYMORPHS OF 4-[3-CHLORO-4-(N'-CYCLOPROPYL UREIDO)PHENOXY] -7-METH-OXYQUINOLINE-6-CARBOXAMIDE, ITS SALTS AND PROCESS FOR THE PREPARATION THEREOF

RELATED APPLICATION

This application is a U.S. National Stage application of PCT International Patent Application Number PCT/IN2018/050823, which was filed on Dec. 8, 2018, which claims priority to Indian patent application numbers 201741044293 filed on Dec. 9, 2017; 201841007887 filed on Mar. 2, 2018 and 201841020743 filed on Jun. 2, 2018, the disclosures of all of which are incorporated by reference in their entirety.

FIELD OF THE INVENTION

The present invention relates to novel polymorphs of 4-[3-chloro-4-(N'-cyclopropylureido)phenoxy]-7-methoxyquinoline-6-carboxamide methanesulfonate represented by following structural formula-1a and process for preparation thereof.

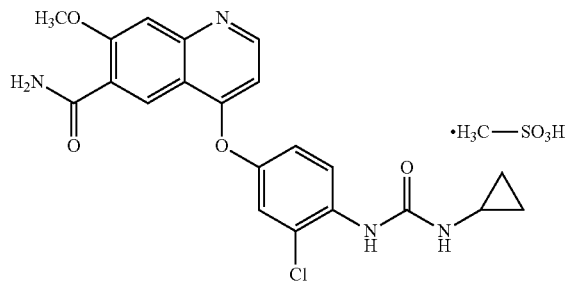

Formula-1a

Further, the present invention relates to an improved process for the preparation of 4-[3-chloro-4-(N'-cyclopropylureido)phenoxy]-7-methoxyquinoline-6-carboxamide compound of formula-1 or its salts. The structure of compound of formula-1 is as follows:

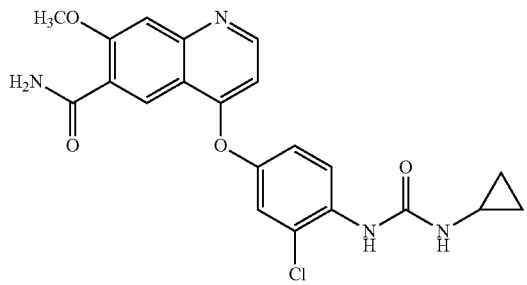

Formula-1

BACKGROUND OF THE INVENTION

4-[3-chloro-4-(N'-cyclopropylureido)phenoxy]-7-methoxyquinoline-6-carboxamide methanesulfonate compound of formula-1a is commonly known as Lenvatinib mesylate, which was approved in US & Europe under the brand name of LENVIMA for the treatment of certain kinds of thyroid cancer. The structure of the formula-1a is as follows:

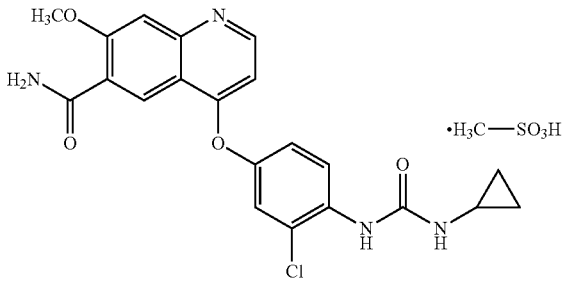

Formula-1a

4-[3-chloro-4-(N'-cyclopropylureido)phenoxy]-7-methoxyquinoline-6-carboxamide compound of formula-1 or salts are disclosed for the first time in U.S. Pat. No. 7,253,286 B2 herein after US'286.

U.S. Pat. No. 7,612,208 B2 describes the crystalline forms of A, B, C, F, and I of 4-[3-chloro-4-(N'-cyclopropylureido) phenoxy]-7-methoxyquinoline-6-carboxamide methanesulfonate and process for its preparation.

U.S. Pat. No. 7,550,483 B2 describes the amorphous form of 4-[3-chloro-4-(N' cyclopropylureido) phenoxy]-7-methoxyquinoline-6-carboxamide methanesulfonate and process for its preparation.

Still, there is a significant need to develop improved process of preparation of and polymorphs of 4-[3-chloro-4-(N' cyclopropylureido)phenoxy]-7-methoxyquinoline-6-carboxamide methanesulfonate which are advantageous over prior art forms to meet the pharmaceuticals requirements.

Since the development of new polymorphic forms of an active pharmaceutical ingredient provides new opportunity to improve the performance characteristics of pharmaceutical finished products, the development of new polymorphic forms is always encouraged.

Furthermore, solid state study of an active pharmaceutical ingredient aims to widen the variety of crystalline forms that a formulation scientist has available for designing a pharmaceutical dosage form with desired characteristics.

After numerous trials and earnest efforts, the present inventors surprisingly found novel crystalline polymorph of 4-[3-chloro-4-(N'-cyclopropylureido)phenoxy]-7-methoxyquinoline-6-carboxamide methanesulfonate having advantageous properties which is useful and suitable for the preparation of various pharmaceutical compositions.

The present inventors also developed an improved process for the preparation of 4-chloro-7-methoxyquinoline-6 carboxamide which is used as key intermediate in the preparation compound of formula-1 or its salts.

US'286 patent discloses process for the preparation of 4-[3-chloro-4-(N'-cyclopropylureido)phenoxy]-7-methoxyquinoline-6-carboxamide via 4-chloro-7-methoxyquinoline-6-carboxamide. The said patent discloses the process for preparation of 4-chloro-7-methoxyquinoline-6-carboxamide from its acid.

Journal of Medicinal Chemistry 2008, 51, 1649-1667 also discloses the process for the preparation of 4-chloro-7-methoxyquinoline-6-carboxamide from its acid as follows:

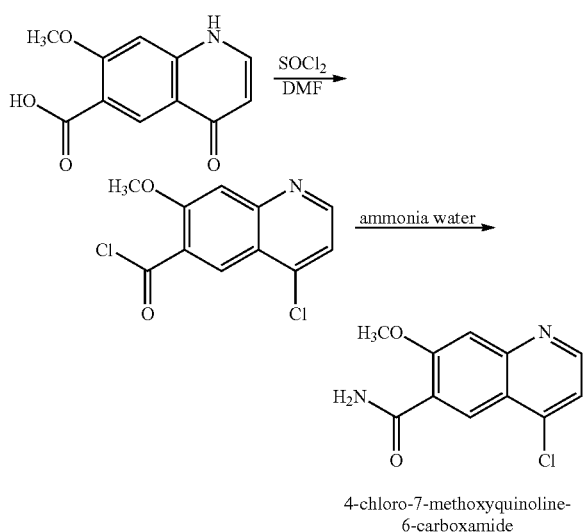

EP 1724268 A1 discloses a process for the preparation of 4-chloro-7-methoxyquinoline-6-carboxamide from its ester as shown in the scheme given below:

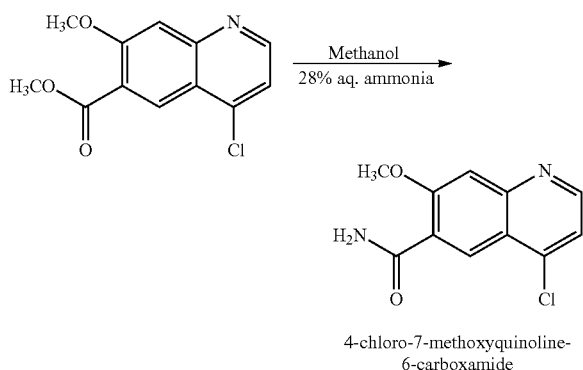

The use of aqueous ammonia destroys the acid chloride formed giving back the acid which results in poor yield of 4-chloro-7-methoxyquinoline-6-carboxamide. The present inventors developed an improved process for the preparation of 4-chloro-7-methoxyquinoline-6-carboxamide with high yield and high purity which is useful in the preparation of the compound of formula-1 and its salts.

BRIEF DESCRIPTION OF THE INVENTION

The first aspect of the present invention is to provide a novel crystalline form of 4-[3-chloro-4-(N'-cyclopropylureido)phenoxy]-7-methoxyquinoline-6-carboxamide methanesulfonate compound of formula-1a, herein after designated as crystalline form-S and process for its preparation.

The second aspect of the present invention is to provide a novel crystalline form of 4-[3-chloro-4-(N'-cyclopropylureido)phenoxy]-7-methoxyquinoline-6-carboxamide methanesulfonate compound of formula-1a, herein after designated as crystalline form-N and process for its preparation.

The third aspect of the present invention is to provide a novel crystalline form of 4-[3-chloro-4-(N'-cyclopropylureido)phenoxy]-7-methoxyquinoline-6-carboxamide methanesulfonate compound of formula-1a, herein after designated as crystalline form-N1 and process for its preparation.

The fourth aspect of the present invention is to provide a novel crystalline form of 4-[3-chloro-4-(N'-cyclopropylureido)phenoxy]-7-methoxyquinoline-6-carboxamide methanesulfonate compound of formula-1a, herein after designated as crystalline form-N2 and process for its preparation.

The fifth aspect of the present invention is to provide a novel crystalline form of 4-[3-chloro-4-(N'-cyclopropylureido)phenoxy]-7-methoxyquinoline-6-carboxamide methanesulfonate compound of formula-1a, herein after designated as crystalline form-L and process for its preparation.

The sixth aspect of the present invention is to provide a novel crystalline form of 4-[3-chloro-4-(N'-cyclopropylureido)phenoxy]-7-methoxyquinoline-6-carboxamide methanesulfonate compound of formula-1a, herein after designated as crystalline form-L1 and process for its preparation.

The seventh aspect of the present invention is to provide an improved process for the preparation of 4-chloro-7-methoxyquinoline-6-carboxamide compound of formula-7.

The eighth aspect of the present invention is to provide an improved process for the preparation of 4-[3-chloro-4-(N'-cyclopropylureido)phenoxy]-7-methoxyquinoline-6-carboxamide compound of formula-1 or its pharmaceutically acceptable salts.

The ninth aspect of the present invention is to provide an improved process for the purification of 4-[3-chloro-4-(N'-cyclopropylureido)phenoxy]-7-methoxyquinoline-6-carboxamide compound of formula-1 or its pharmaceutically acceptable salts.

BRIEF DESCRIPTION OF THE DRAWINGS

FIG. 1 Illustrates the powder X-Ray diffraction pattern of crystalline form-S of compound of formula-1a.

FIG. 2 Illustrates the DSC thermogram of crystalline form-S of compound of formula-1a.

FIG. 5 Illustrates the powder X-Ray diffraction pattern of crystalline form-N1 of compound of formula-1a.

FIG. 6 Illustrates the powder X-Ray diffraction pattern of crystalline form-N2 of compound of formula-1a.

FIG. 7 Illustrates the DSC thermogram of crystalline form-N2 of compound of formula-1a.

FIG. 8 Illustrates the powder X-Ray diffraction pattern of crystalline form-L of compound of formula-1a.

FIG. 9 Illustrates the powder X-Ray diffraction pattern of crystalline form-L1 of compound of formula-1a.

DETAILED DESCRIPTION OF THE INVENTION

Figure 1:
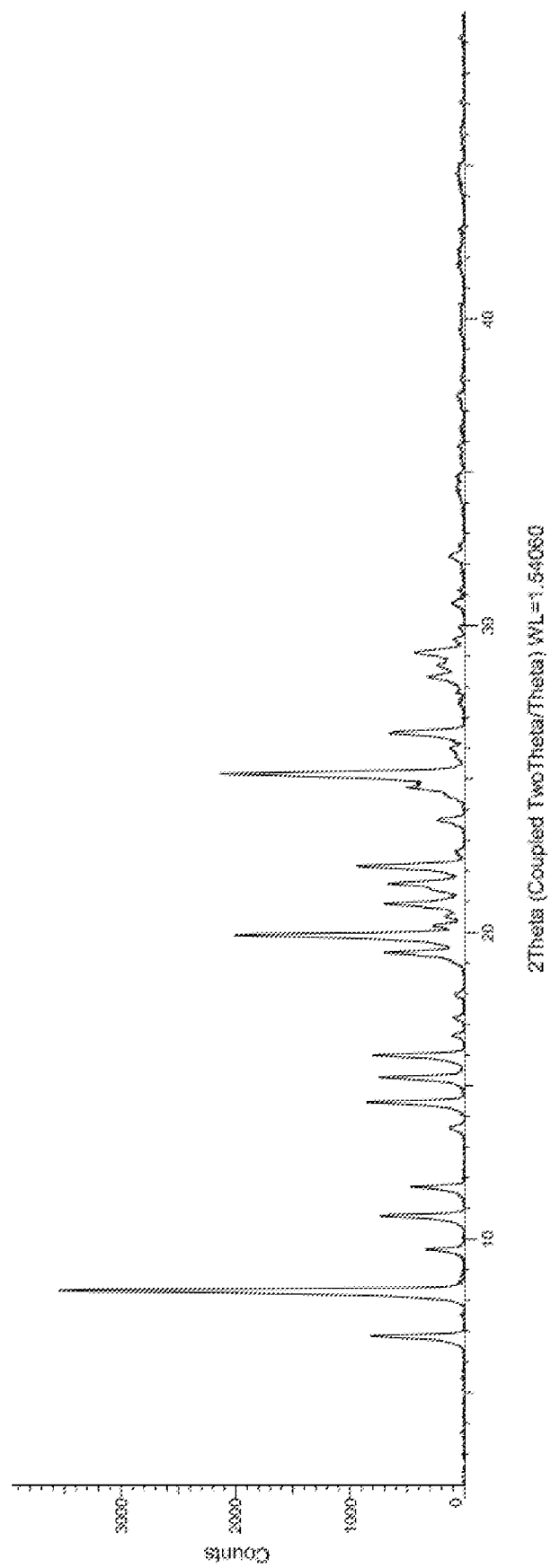

As used herein the term "suitable solvent" in the present invention refers to "hydrocarbon solvents" such as n-hexane, n-heptane, cyclohexane, pet ether, benzene, toluene, pentane, cycloheptane, methyl cyclohexane, ethylbenzene, m-, o-, or p-xylene, or naphthalene and the like; "ether solvents" such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethyl sulfoxide (DMSO), N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcohol solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, 1,2-propanediol (propylene glycol), 2-methoxyethanol, 1,2-ethoxyethanol, diethylene glycol, 1, 2, or 3-pentanol, neo-pentyl alcohol, t-pentyl alcohol, diethylene glycol monoethyl ether, cyclohexanol, benzyl alcohol, phenol, or glycerol and the like; "polar solvents" such as water or mixtures thereof.

As used herein the term "suitable base" in the present invention refers to inorganic bases like "alkali metal carbonates" such as sodium carbonate, potassium carbonate, lithium carbonate and the like; "alkali metal bicarbonates" such as sodium bicarbonate, potassium bicarbonate and the like; "alkali metal hydroxides" such as sodium hydroxide, potassium hydroxide, lithium hydroxide and the like; alkali metal hydrides such as sodium hydride, potassium hydride, lithium hydride and the like; alkali metal amides such as sodium amide, potassium amide, lithium amide and the like; ammonia such as aqueous ammonia, ammonia gas, alcoholic ammonia; and organic bases like dimethylamine, diethylamine, diisopropyl amine, diisopropylethylamine, diisobutylamine, triethylamine, pyridine, 4-dimethylaminopyridine (DMAP), N-methyl morpholine (NMM), 2,6-lutidine, lithium diisopropylamide; "alkali metal alkoxides" such as sodium methoxide, sodium ethoxide, potassium methoxide, potassium ethoxide, sodium tert.butoxide, potassium tert.butoxide, lithium tert.butoxide and the like; organosilicon bases such as lithium hexamethyldisilazide (LiHMDS), sodium hexamethyldisilazide (NaHMDS), potassium hexamethyldisilazide (KHMDS) or mixtures thereof.

As used herein the term "its pharmaceutically acceptable salts" or "salts" in the present invention refers to acid addition salts selected from inorganic acids such as hydrochloric acid, hydrobromic acid, sulfuric acid, nitric acid, phosphoric acid; organic acids such as acetic acid, maleic acid, malic acid, oxalic acid, trifluoroacetic acid, methane sulfonic acid, p-toluene sulfonic acid; chiral acids such as S-(+) mandelic acid, R-(−) mandelic acid, L-(+)tartaric acid, D-(−)tartaric acid, L-malic acid, D-malic acid, D-maleic acid, (−)-naproxen, (+)-naproxen, (lR)-(−)-camphor sulfonic acid, (1S)-(+)-camphor sulfonic acid (lR)-(+)-bromocamphor-10-sulfonic acid, (1S)-(−)-bromocamphor-10-sulfonic acid, (−)-Dibenzoyl-L-tartaric acid, (−)-Dibenzoyl-L-tartaricacid monohydrate, (+)-Dibenzoyl-D-tartaric acid, (+)-Dibenzoyl-D-tartaric acid monohydrate, (+)-dipara-tolyl-D-tataric acid, (−)-dipara-tolyl-L-tataricacid, L-(−)-pyroglutamic acid, L(+)-pyroglutamic acid, (−)-lactic acid, L-lysine, D-lysine etc., and like.

As used herein the term suitable "chlorinating agent" include but are not limited to chlorine, oxalyl chloride, sulfuryl chloride, thionyl chloride, phosphorus oxychloride, phosphorus pentachloride, pivaloyl chloride, antimony pentachloride, iodine trichloride, sulfur dichloride, disulfur dichloride, manganese tetrachloride and the like.

As used herein the term suitable "trialkyl orthoformate" include but are not limited to trimethyl orthoformate, triethyl orthoformate, tri butyl orthoformate and the like; in particular triethyl orthoformate.

As used herein the term suitable "carbonylating reagent" include but are not limited to 1,1'-carbonyldiimidazole, 4-nitrophenyl chloroformate, diphosgene, triphosgene, phenyl chloroformate, benzyl chloroformate and the like.

As used herein the terms "DSC" refers to Differential scanning calorimetry; "PXRD" refers to powder X-Ray diffractogram; "DMSO" refers to dimethyl sulfoxide or dimethylsulfoxide.

Figure 2:
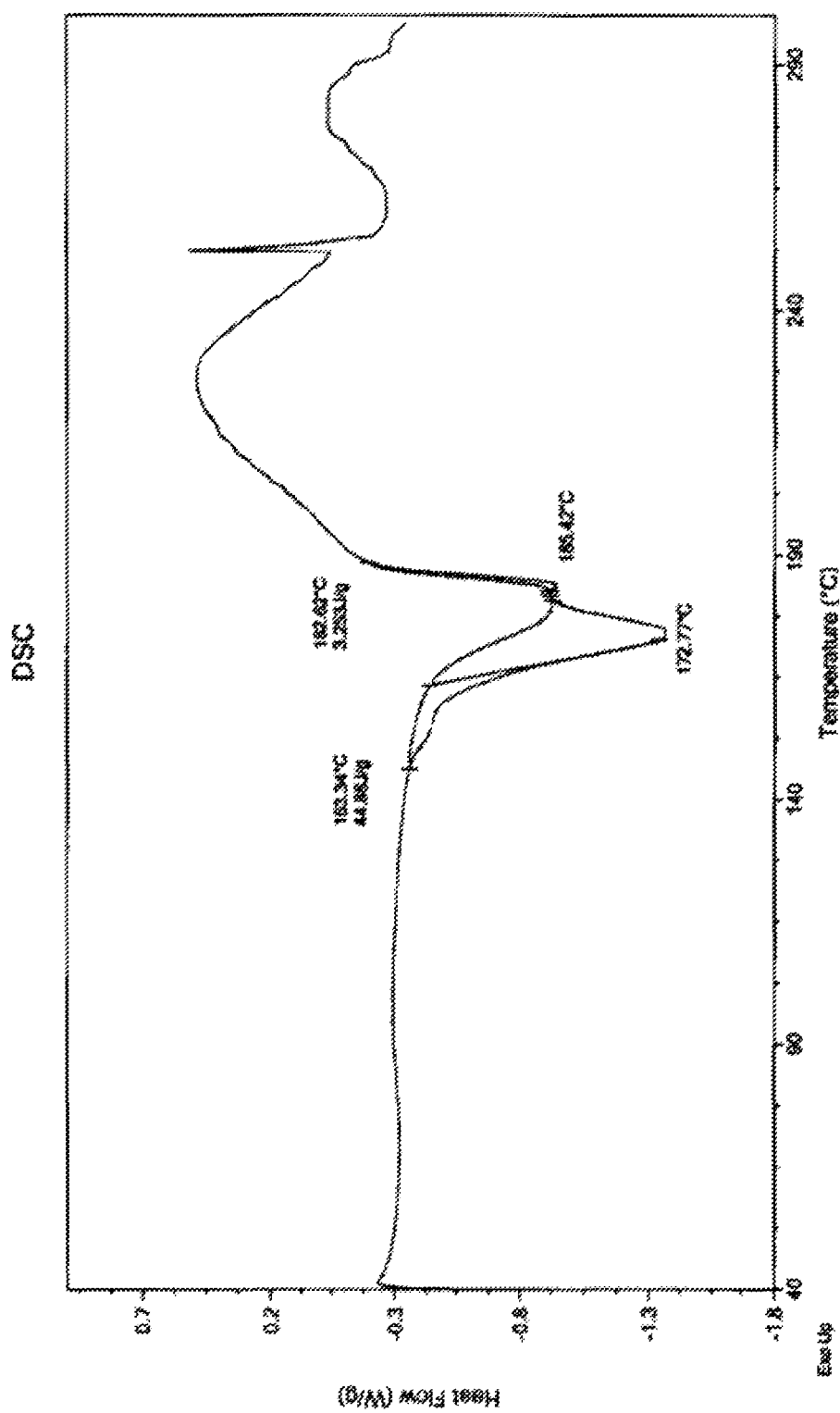

The first aspect of the present invention provides novel crystalline form of 4-[3-chloro-4-(N'-cyclopropylureido) phenoxy]-7-methoxyquinoline-6-carboxamide methanesulfonate compound of formula-1a, herein after designated as crystalline form-S. The said crystalline form-S of formula-1a characterized by:
a) its PXRD pattern substantially in accordance with FIG. 1,
b) its powder X-Ray diffractogram having peaks at 6.8, 8.3, 10.7, 14.4, 15.2, 16.0, 19.9, 25.1 and 26.5±0.2 degrees of two-theta, and/or
c) its DSC thermogram as illustrated in FIG. 2.

Further aspect of the present invention provides a process for the preparation of crystalline form-S of compound of formula-1a, comprising:
a) dissolving the compound of formula-1a in a suitable solvent at a suitable temperature,
b) optionally combining the solution with a suitable second solvent at a suitable temperature,
c) isolating the crystalline form-S of compound of formula-1a.

A suitable solvent in step-a) is selected from alcohol solvents, ester solvents, chloro solvents, nitrile solvents, ketone solvents, polar solvents, water or mixtures thereof; suitable temperature ranges from 25° C. to reflux temperature of the solvent used; suitable second solvent in step-b) is different from the solvent used in step-a), selected from alcohol solvents, ether solvents, ester solvent, chloro solvents, nitrile solvents, hydrocarbon solvents, polar aprotic solvents, ketone solvents or mixtures thereof; suitable temperature ranges from −20 to 30° C.; isolating in step-c) is by solvent removal by known techniques which are selected from but not limited to distillation, decanting, filtration or cooling the mixture to lower temperatures to precipitate the solid followed by filtration of the mixture.

The second aspect of the present invention provides novel crystalline form of 4-[3-chloro-4-(N'-cyclopropylureido) phenoxy]-7-methoxyquinoline-6-carboxamide methanesulfonate compound of formula-1a, herein after designated as crystalline form-N.

Figure 3:
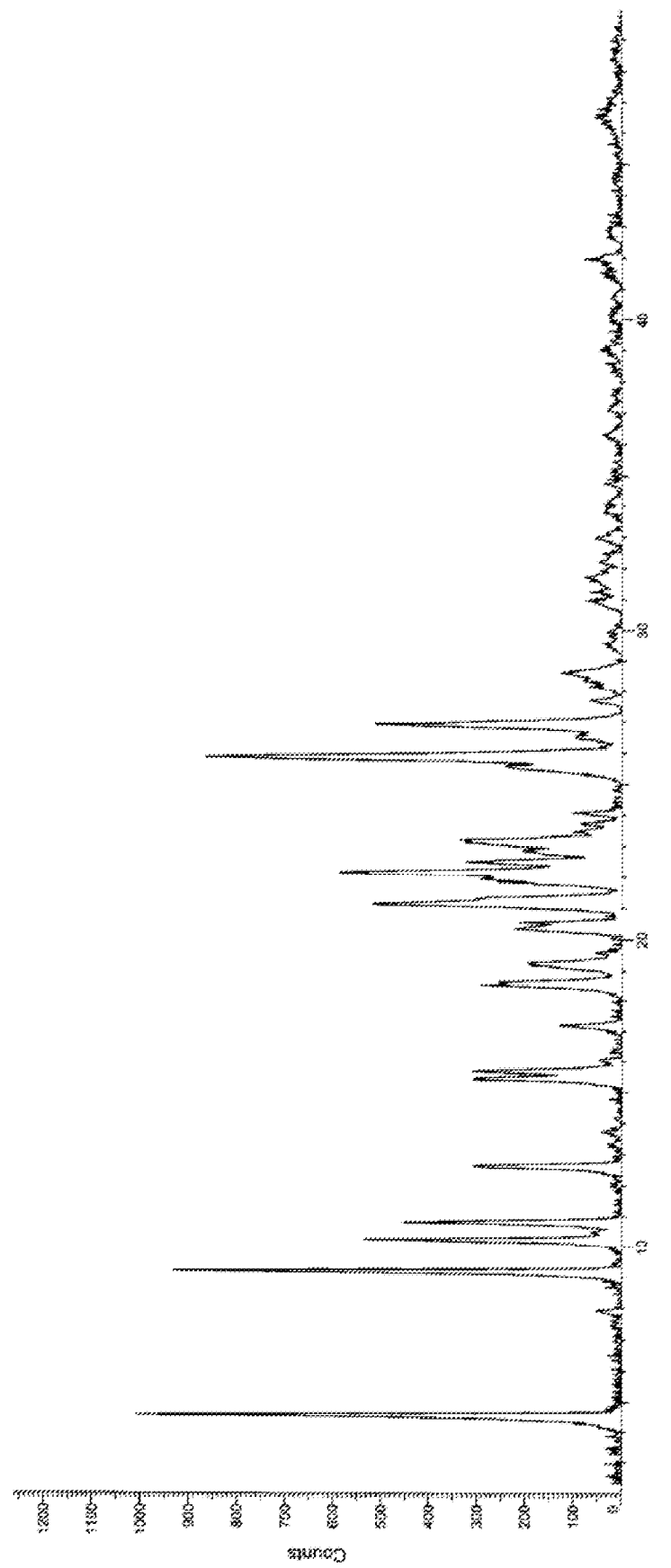
FIG. 3 Illustrates the powder X-Ray diffraction pattern of crystalline form-N of compound of formula-1a obtained according to Example-2.
Figure 4:
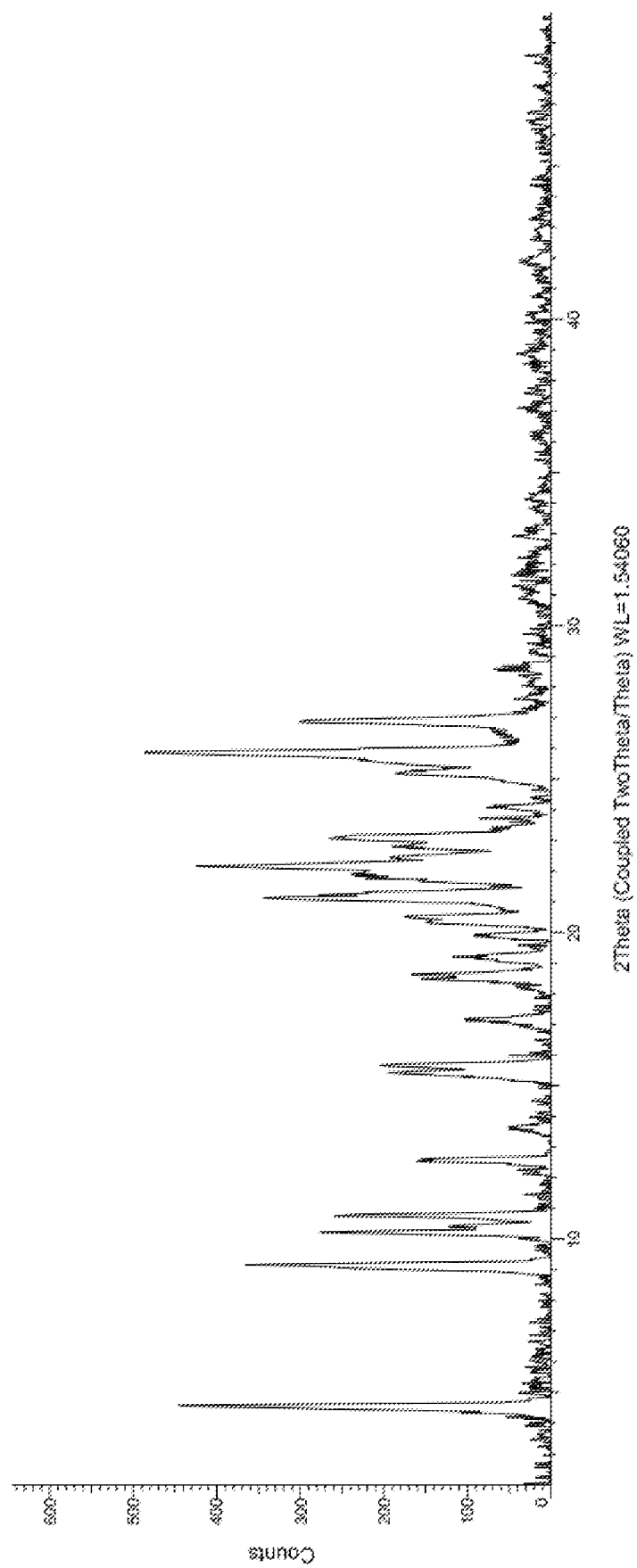
FIG. 4 Illustrates the powder X-Ray diffraction pattern of crystalline form-N of compound of formula-1a obtained according to Example-3.

The said crystalline form-N of formula-1a characterized by:
a) its PXRD pattern substantially in accordance with FIG. 3 and/or FIG. 4, and/or
b) its powder X-Ray diffractogram having peaks at 4.5, 9.1, 10.2, 10.7, 15.4, 15.6, 21.1, 22.1 and 25.8±0.2 degrees of two-theta.

Further aspect of the present invention provides a process for the preparation of crystalline form-N of compound of formula-1a, comprising:
a) dissolving the compound of formula-1a in dimethyl sulfoxide or in the mixture of dimethyl sulfoxide and a suitable solvent at a suitable temperature,
b) optionally combining the solution with a suitable second solvent at a suitable temperature,
c) isolating the crystalline form-N of 4-[3-chloro-4-(N'-cyclopropylureido)phenoxy]-7-methoxyquinoline-6-carboxamide methanesulfonate compound of formula-1a.

A suitable solvent in step-a) is selected from alcohol solvents, ester solvents, chloro solvents, nitrile solvents, ketone solvents, polar solvents, water or mixtures thereof; suitable temperature ranges from 25° C. to reflux temperature of the solvent used; suitable second solvent in step-b) is different from the solvent used in step-a), selected from alcohol solvents, ether solvents, ester solvent, chloro solvents, nitrile solvents, hydrocarbon solvents, polar aprotic solvents, ketone solvents or mixtures thereof; suitable temperature ranges from −20 to 30° C.; isolating in step-c) is by solvent removal by known techniques which are selected from but not limited to distillation, decanting, filtration or cooling the mixture to lower temperatures to precipitate the solid followed by filtration of the mixture.

Further aspect of the present invention provides another process for the preparation of crystalline form-N of compound of formula-1a, comprising:
a) adding compound of formula-1 to dimethyl sulfoxide or mixture of dimethyl sulfoxide and a suitable solvent,
b) heating the mixture to a suitable temperature,
c) adding methane sulfonic acid to the mixture obtained in step-b),
d) optionally adding a suitable second solvent to the mixture obtained in step-c), e) isolating crystalline form-N of compound of formula-1a.

A suitable solvent in step-a) is selected from alcohol solvents, ester solvents, chloro solvents, nitrile solvents, ketone solvents, polar solvents, water or mixtures thereof; suitable temperature in step-b) ranges from 25° C. to reflux temperature of the solvent used; suitable second solvent in step-d) is different from the solvent used in step-a), selected from alcohol solvents, ether solvents, ester solvent, chloro solvents, nitrile solvents, hydrocarbon solvents, polar aprotic solvents, ketone solvents or mixtures thereof; isolating in step-e) is by solvent removal by known techniques which are selected from but not limited to distillation, decanting, filtration or cooling the mixture to lower temperatures to precipitate the solid followed by filtration of the mixture.

Preferred embodiment of the present invention provides a process for the preparation of crystalline form-N of compound of formula-1a, comprising:
a) dissolving compound of formula-1a in a mixture of dimethyl sulfoxide and water at 70 to 80° C.,
b) cooling the solution obtained in step-a) to 0-5° C.,
c) combining the solution obtained in step-b) with pre-cooled methyl isobutyl ketone, d) filtering the solid obtained in step-c) to provide the crystalline form-N of compound of formula-1a.

Further Preferred embodiment of the present invention provides a process for the preparation of crystalline form-N of compound of formula-1a, comprising:
a) dissolving compound of formula-1 in dimethyl sulfoxide at 60 to 70° C.,
b) adding methane sulfonic acid and isopropanol to the solution obtained in step-a),
c) optionally cooling the solution obtained in step-b) to 10-15° C.,
d) filtering the solid obtained in step-c) to provide the crystalline form-N compound of formula-1a.

The third aspect of the present invention provides novel crystalline form of 4-[3-chloro-4-(N'-cyclopropylureido)phenoxy]-7-methoxyquinoline-6-carboxamide methanesulfonate compound of formula-1a, herein after designated as crystalline form-N1. The said crystalline form-N1 of formula-1a characterized by:
a) its PXRD pattern substantially in accordance with FIG. 5, and/or
b) its powder X-Ray diffractogram having peaks at 4.5, 6.6, 8.1, 9.0, 10.2, 10.6, 14.2, 15.2, 15.6, 19.7, 21.9, 22.8, 24.9, 25.7, 26.8±0.2 degrees of two-theta.

Further aspect of the present invention provides a process for the preparation of crystalline form-N1 of compound of formula-1a, comprising:
a) dissolving compound of formula-1a in dimethyl sulfoxide or in mixture of dimethyl sulfoxide and a suitable solvent at a suitable temperature,
b) optionally combining the solution with a suitable second solvent at a suitable temperature,
c) isolating crystalline form-N1 of compound of formula-1a.

A suitable solvent in step-a) is selected from alcohol solvents, ester solvents, chloro solvents, nitrile solvents, ketone solvents, polar solvents or mixtures thereof; suitable temperature ranges from 25° C. to reflux temperature of the solvent used; suitable second solvent in step-b) is different from the solvent used in step-a), selected from alcohol solvents, ether solvents, ester solvent, chloro solvents, nitrile solvents, hydrocarbon solvents, polar aprotic solvents, ketone solvents or mixtures thereof; suitable temperature ranges from −20 to 30° C.; isolating in step-c) is by solvent removal by known techniques which are selected from but not limited to distillation, decanting, filtration or cooling the mixture to lower temperatures to precipitate the solid followed by filtration of the mixture.

The fourth aspect of the present invention provides novel crystalline form of 4-[3-chloro-4-(N'-cyclopropylureido)phenoxy]-7-methoxyquinoline-6-carboxamide methanesulfonate compound of formula-1a, herein after designated as crystalline form-N2.

Figure 6:
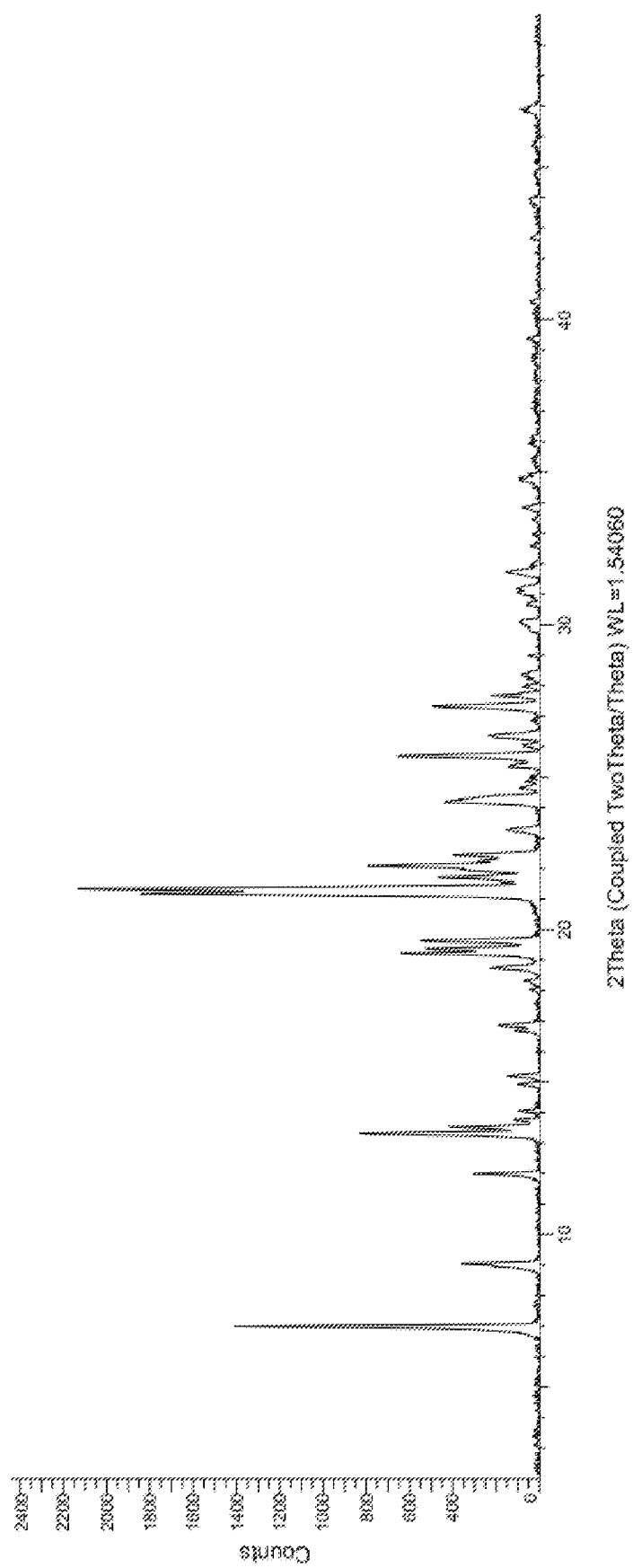
Figure 7:
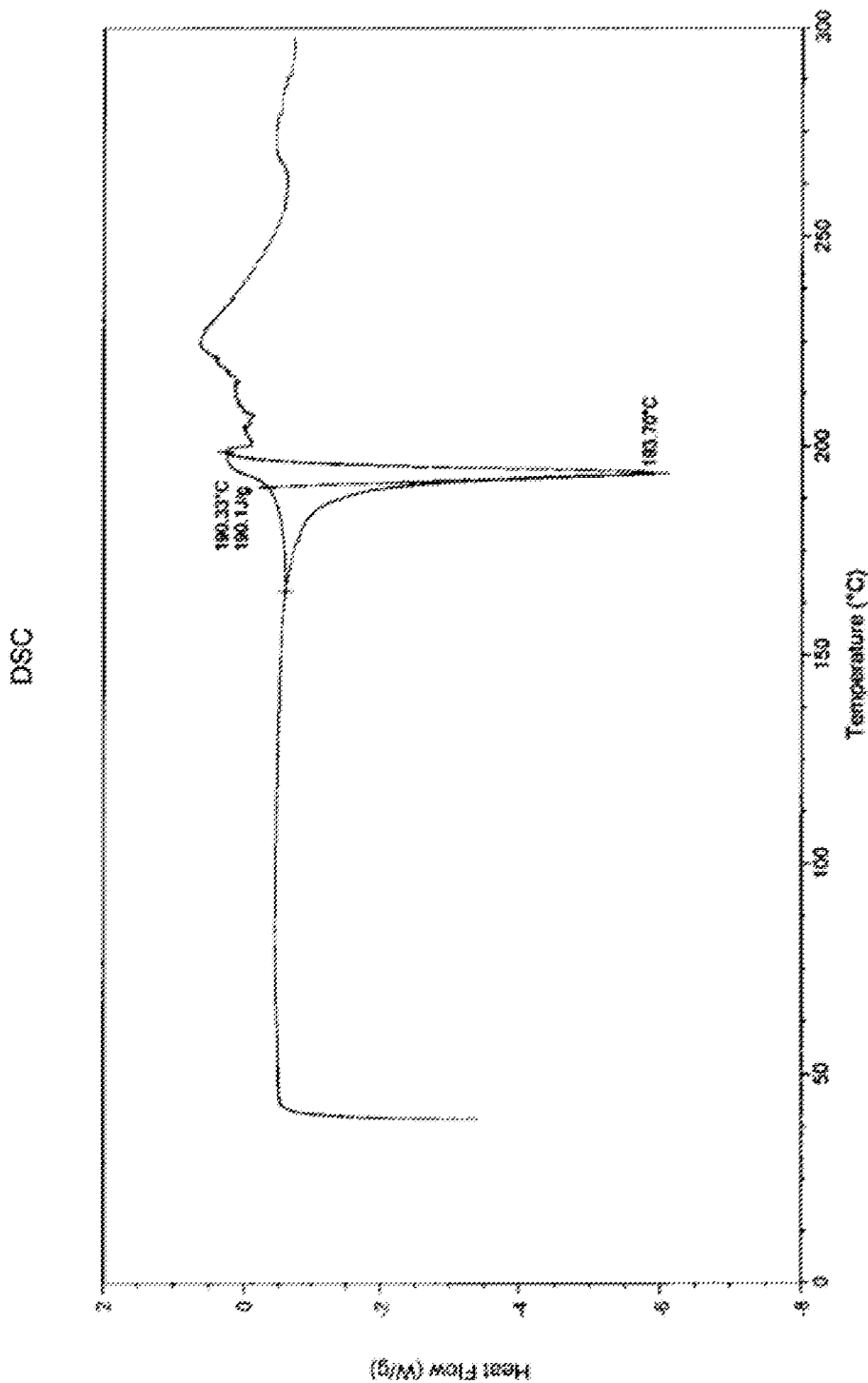

The crystalline form-N2 of the present invention can be characterized by one or more of the following characteristics:
a) PXRD pattern substantially in accordance with FIG. 6,
b) powder X-Ray diffractogram having peaks at about 7.0, 8.9, 9.0, 12.0, 13.3, 13.5, 19.2, 21.2, 21.3, 22.1, 24.2 and 25.7±0.2 degrees of two-theta,
c) DSC thermogram as illustrated in FIG. 7,
d) DSC having endotherm peak at about 192±3° C.,
e) having DMSO content in the range of 10 to 20%.

In another aspect of the present invention provides crystalline form-N2 which is a DMSO solvate of compound of formula-1a.

In another aspect of the present invention provides crystalline form-N2 which is a DMSO solvate of compound of formula-1a is structurally shown as follows:

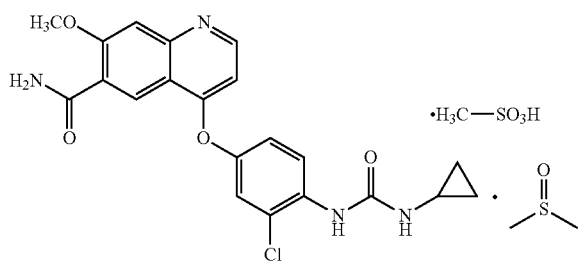

Further aspect of the present invention provides a process for the preparation of crystalline form-N2 of compound of formula-1a, comprising:
a) adding compound of formula-1 to a suitable solvent comprising dimethyl sulfoxide,
b) optionally heating the mixture to a suitable temperature,
c) adding methane sulfonic acid to the mixture obtained in step-a) or step-b),
d) optionally combining the mixture obtained in step-c) with a second solvent,
e) isolating crystalline form-N2 of compound of formula-1a.

A suitable solvent in step-a) is selected from alcohol solvents, ester solvents, chloro solvents, nitrile solvents, ketone solvents, polar solvents, water or mixtures thereof; the heating temperature in step-b) is about 0° C. to about 100° C. or about 25° C. to about 80° C. or about 40° C. to about 70° C. or about 60° C. to about 70° C. or any other suitable temperature; second solvent in step-d) is different from solvent used in step-a), selected from alcohol solvents, ether solvents, ester solvent, chloro solvents, nitrile solvents, hydrocarbon solvents, polar aprotic solvents, ketone solvents or mixtures thereof; isolating in step-e) is by solvent removal by known techniques which are selected from but not limited to distillation, decanting, filtration or cooling the mixture to lower temperatures to precipitate the solid followed by filtration of the mixture.

Further aspect of the present invention provides a process for the preparation of crystalline form-N2 of compound of formula-1a, comprising:
a) providing a solution of compound of formula-1a in a suitable solvent comprising dimethyl sulfoxide,
b) isolating the solid to provide crystalline form-N2 of compound of formula-a.

A solution of compound of formula-1a in step-a) is by combining compound of formula-1 with methane sulphonic in a suitable solvent comprising dimethyl sulfoxide or by dissolving compound of formula-1a in a suitable solvent comprising dimethyl sulfoxide. Methane sulfonic acid can be added to compound of formula-1 either in the form of a solid or as a solution in a suitable solvent. The resulting mixture of compound of formula-1 with methane sulfonic acid or a compound of formula-1a can be optionally heated to a suitable temperature to provide the said solution. The suitable temperature can be about 0° C. to about 100° C. or about 25° C. to about 80° C. or about 40° C. to about 70° C. or about 60° C. to about 70° C. or any other suitable temperature. A suitable solvent in step-a) is selected from alcohol solvents, ester solvents, chloro solvents, nitrile solvents, ketone solvents, polar solvents, water or mixtures thereof. Isolating in step-b) is by solvent removal by known techniques which are selected from distillation, decanting, filtration, cooling the mixture to lower temperatures to precipitate the solid followed by filtration of the mixture, crystallization or by adding suitable second solvent which is different from the solvent used in step-a), selected from but not limited to alcohol solvents, ester solvents, chloro solvents, nitrile solvents, ketone solvents, polar solvents, water or mixtures thereof.

Preferred embodiment of the present invention provides a process for the preparation of crystalline form-N2 of compound of formula-1a, comprising:
a) adding methane sulfonic acid to the mixture of compound of formula-1 and dimethyl sulfoxide,
b) optionally the solution obtained in step-a) seeding with crystalline form-N2 of compound of formula-1a,
c) combining the mixture obtained in step-b) with isobutyl acetate,
d) filtering the solid obtained in step-c) to provide crystalline form-N2 of compound of formula-1a.

Further aspect of the present invention provides crystalline DMSO solvate of the compound of formula-1a having particle size distribution of D90 is about <500 μm, preferably about <300 μm, more preferably about <100 μm; D50 is about <150 μm, preferably about <100 μm, more preferably about <50 μm and D10 is about <50 μm, preferably about <20 μm, more preferably about <15 μm.

The fifth aspect of the present invention provides novel crystalline form of 4-[3-chloro-4-(N'-cyclopropylureido) phenoxy]-7-methoxyquinoline-6-carboxamide methanesulfonate compound of formula-1a, herein after designated as crystalline form-L of compound of formula-1a. The said crystalline form-L of formula-1a characterized by:
a) its PXRD pattern substantially in accordance with FIG. 8, and/or
b) its powder X-Ray diffractogram having peaks at 4.4, 8.9, 10.4, 10.7, 17.0, 15.6, 21.8, 25.0±0.2 degrees of two-theta.

Further aspect of the present invention provides a process for the preparation of crystalline form-L of compound of formula-1a, comprising:
a) dissolving the compound of formula-1a in a suitable solvent at a suitable temperature,
b) optionally combining the solution with a suitable second solvent at a suitable temperature,
c) isolating crystalline form-L of compound of formula-1a.

A suitable solvent in step-a) is selected from alcohol solvents, ester solvents, chloro solvents, nitrile solvents, ketone solvents, polar solvents or mixtures thereof; suitable temperature ranges from 25° C. to reflux temperature of the solvent used; suitable second solvent in step-b) is different from the solvent used in step-a), selected from alcohol solvents, ether solvents, ester solvent, chloro solvents, nitrile solvents, hydrocarbon solvents, polar aprotic solvents, ketone solvents or mixtures thereof; suitable temperature ranges from −20 to 30° C.; isolating in step-c) is by solvent removal by known techniques which are selected from but not limited to distillation, decanting, filtration or cooling the mixture to lower temperatures to precipitate the solid followed by filtration of the mixture.

Figure 9:
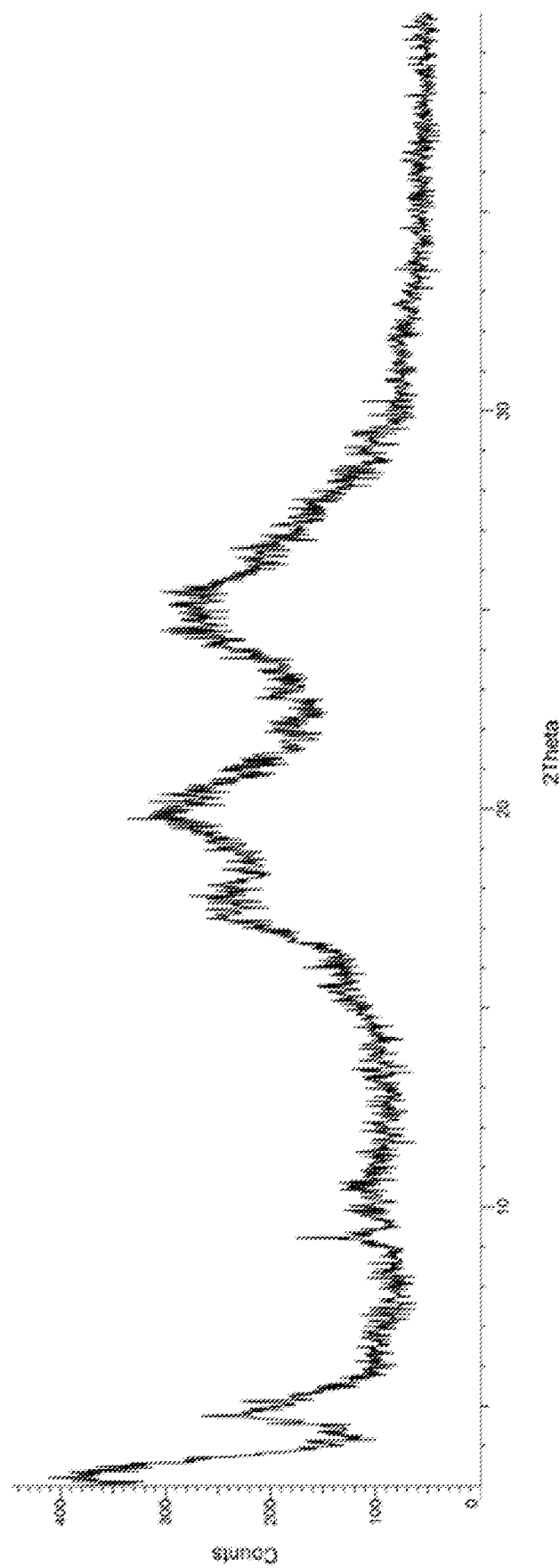

The sixth aspect of the present invention provides novel crystalline form of 4-[3-chloro-4-(N'-cyclopropylureido) phenoxy]-7-methoxyquinoline-6-carboxamide methanesulfonate compound of formula-1a, herein after designated as crystalline form-L1 of compound of formula-1a. The said crystalline form-L1 of formula-1a characterized by:

a) its PXRD pattern substantially in accordance with FIG. 9, and/or b) its powder X-Ray diffractogram having peaks at 4.7, 9.2, 9.4, 10.0, 17.3, 20.5, 21.0, 22.8, 28.2, 29.4±0.2 degrees of two-theta.

Further aspect of the present invention provides a process for the preparation of crystalline form-L1 of compound of formula-1a, comprising:

a) dissolving compound of formula-1a in a suitable solvent at a suitable temperature, b) optionally combining the solution with a suitable second solvent at a suitable temperature, c) isolating crystalline form-L1 of compound of formula-1a.

A suitable solvent in step-a) is selected from alcohol solvents, ester solvents, chloro solvents, nitrile solvents, ketone solvents, polar solvents or mixtures thereof; suitable temperature ranges from 25° C. to reflux temperature of the solvent used; suitable second solvent in step-b) is different from the solvent used in step-a), selected from alcohol solvents, ether solvents, ester solvent, chloro solvents, nitrile solvents, hydrocarbon solvents, polar aprotic solvents, ketone solvents or mixtures thereof; suitable temperature ranges from −20 to 30° C.; isolating in step-c) is by solvent removal by known techniques which are selected from but not limited to distillation, decanting, filtration or cooling the mixture to lower temperatures to precipitate the solid followed by filtration of the mixture.

The seventh aspect of the present invention provides an improved process for the preparation of 4-chloro-7-methoxyquinoline-6-carboxamide compound of formula-7, comprising reacting compound of general formula-6 with formamide in presence of a suitable base in a suitable solvent to provide compound of formula-7; wherein suitable base is selected from organic bases or inorganic bases and suitable solvent is selected from alcohol solvents, ketone solvents, nitrile solvents, ether solvents, chloro solvents, polar-aprotic solvents; preferably polar-aprotic solvents.

Preferred embodiment of the present invention provides an improved process for the preparation of 4-chloro-7-methoxyquinoline-6-carboxamide compound of formula-7 comprising reacting compound of formula-6a with formamide in presence of sodium tertiary butoxide in dimethyl formamide to provide compound of formula-7.

The eighth aspect of the present invention provides an improved process for the preparation of 4-[3-chloro-4-(N'-cyclopropylureido)phenoxy]-7-methoxyquinoline-6-carboxamide compound of formula-1 or its salts comprising:

a) reacting 2,2-dimethyl-1,3-dioxane-4,6-dione {Meldrum's acid} compound of formula-2 with trialkyl or triaryl orthoformate and compound of general formula-3

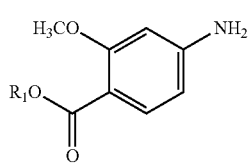

Formula-3

Wherein $R_1$ is selected from $C_{1-6}$ alkyl group, $C_{6-10}$ aryl or aralkyl;

in a suitable solvent to provide compound of general formula-4,

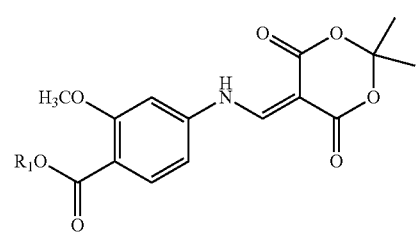

Formula-4 b) converting the compound of general formula-4 to compound of general formula-5 in DOWTHERM A or diphenyl ether,

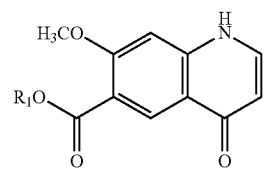

Formula-5

Wherein $R_1$ is selected from $C_{1-6}$ alkyl group, $C_{6-10}$ aryl or aralkyl;

c) reacting compound of general formula-5 with suitable chlorinating agent in a suitable solvent to provide compound of general formula-6,

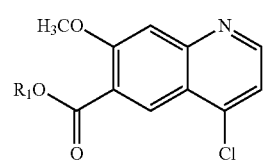

Formula-6

Wherein $R_1$ is selected from $C_{1-6}$ alkyl group, $C_{6-10}$ aryl or aralkyl;

d) reacting compound of general formula-6 with formamide in presence of a suitable base in a suitable solvent to provide 4-chloro-7-methoxyquinoline-6-carboxamide compound of formula-7, e) reacting compound of formula-7 with 4-amino-3-chlorophenol or its salts in the presence of suitable base in a suitable solvent to provide 4-(4-amino-3-chlorophenoxy)-7-methoxyquinoline-6-carboxamide compound of formula-8, f) reacting compound of formula-8 with a suitable carbonylating agent in presence of suitable base in a solvent to provide compound of general formula-9,

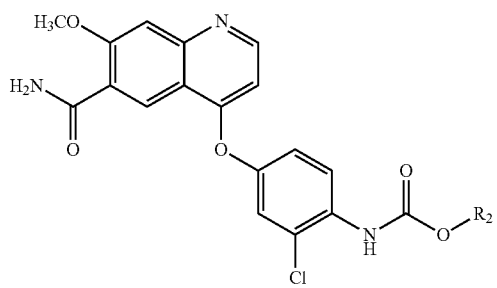

Formula-9

Wherein $R_2$ is selected from alkyl or aryl which is substitute or un substituted;

g) reacting compound of general formula-9 with cyclopropylamine in a suitable solvent to obtain 4-[3-chloro-4-(N'-cyclopropylureido)phenoxy]-7-methoxy quinoline-6-carboxamide compound of formula-1, h) optionally converting the obtained compound of formula-1 into its salts.

A suitable solvent in steps-a) to g) is selected from alcohol solvents, ketone solvents, ester solvents, ether solvents, chloro solvents, nitrile solvents, polar-aprotic solvents, water and/or mixtures thereof; trialkyl or aryl orthoformate in step a) is selected from trimethyl orthoformate, triethyl orthoformate, tri butyl orthoformate, triphenyl orthoformate and the like; chlorinating agent in step-d) is selected from chlorine, oxalyl chloride, sulfuryl chloride, thionyl chloride, phosphorus oxychloride, phosphorus pentachloride, pivaloyl chloride, antimony pentachloride, iodine trichloride, sulfur dichloride, disulfur dichloride, manganese tetrachloride and the like; suitable base in step-e) to g) is selected from organic base or inorganic base; carbonylating reagent in step-f) is selected from 1,1'-carbonyldiimidazole, 4-nitrophenyl chloroformate, diphosgene, triphosgene, phenyl chloroformate, benzyl chloroformate and the like.

The intermediate compounds obtained in the present invention can be optionally purifying using a suitable solvent.

Preferred embodiment of the present invention provides an improved process for the preparation of compound of formula-1a comprising:

a) reacting 2,2-dimethyl-1,3-dioxane-4,6-dione compound of formula-2 with triethyl orthoformate and methyl 4-amino-2-methoxybenzoate in isopropanol to provide compound of formula-4a, b) converting compound of formula-4a to compound of formula-5a in diphenyl ether, c) reacting compound of formula-5a with $POCl_3$ in dichloromethane and dimethyl formamide to provide compound of formula-6a, d) reacting compound of formula-6a with formamide in sodium tertiary butoxide in dimethyl formamide to provide 4-chloro-7-methoxyquinoline-6-carboxamide compound of formula-7, e) reacting compound of formula-7 with 4-amino-3-chlorophenol or its hydrochloride salt in presence of aqueous potassium hydroxide solution in dimethyl sulfoxide to provide compound of formula-8, f) reacting compound of formula-8 with phenyl chloroformate in presence of pyridine and sodium carbonate in dimethyl formamide to provide compound of formula-9a, g) reacting compound of formula-9a with cyclopropylamine in dimethyl formamide to obtain compound of formula-1, h) converting the obtained compound of formula-1 into its methane sulfonic acid salt compound of formula-1a.

The seventh & eighth aspects of the present invention are schematically represented as follows:

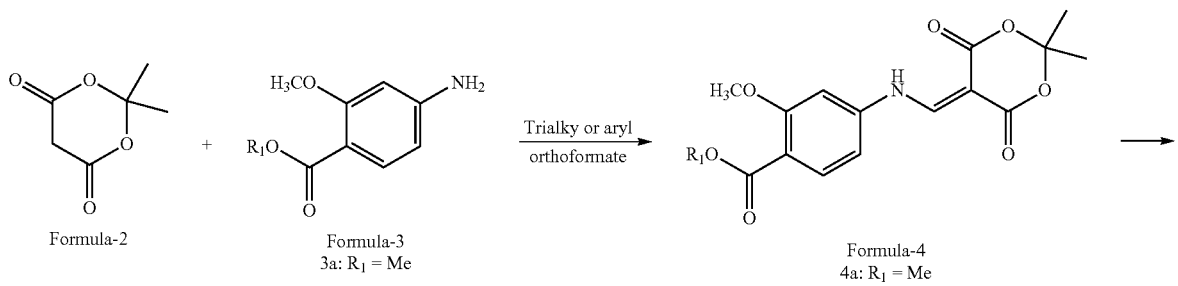

Formula-2

Formula-3
3a: $R_1$ = Me

Trialky or aryl orthoformate

Formula-4
4a: $R_1$ = Me

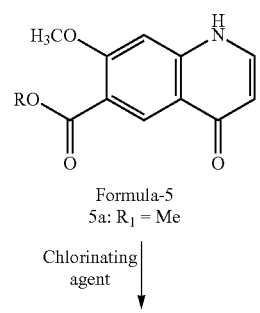

Formula-5
5a: $R_1$ = Me

Chlorinating agent

-continued

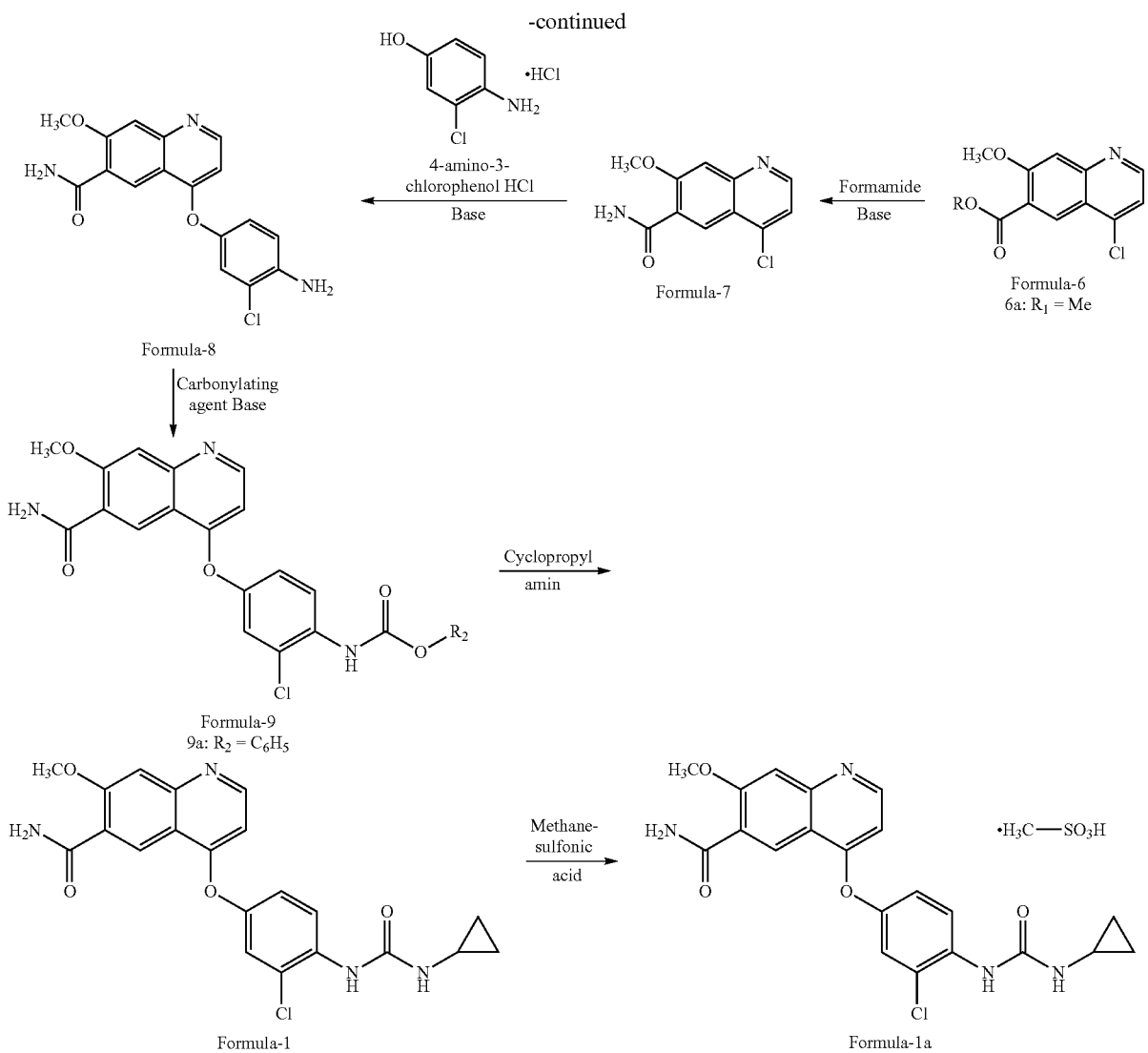

Wherein $R_1$ is selected from $C_{1-6}$ alkyl group, $C_{6-10}$ aryl or aralkyl; $R_2$ is selected from alkyl or aryl which is substitute or unsubstituted The ninth aspect of the present invention provides an improved process for the purification of 4-[3-chloro-4-(N'-cyclopropylureido)phenoxy]-7-methoxyquinoline-6-carboxamide compound of formula-1 or its pharmaceutically acceptable salts comprising:
a) adding compound of formula-1 or its pharmaceutically acceptable salts to a suitable solvent or mixture of solvents,
b) optionally heating the reaction mixture obtained in step-a) to a suitable temperature,
c) optionally adding the second solvent to the mixture obtained in step-a) or step-b) at a suitable temperature,
d) isolating substantially pure compound of formula-1 or its pharmaceutically acceptable salts.

A suitable solvent in step-a) is selected from polar-aprotic solvents, alcohol solvents, ether solvents, ester solvents, chloro solvents, ketone solvents, polar solvents such as water or mixtures thereof; suitable temperature in step-b) ranges from 30° C. to reflux temperature of the solvent used; suitable second solvent in step-c) is different from the solvent used in step-a), selected from alcohol solvents, ether solvents, ester solvent, chloro solvents, nitrile solvents, hydrocarbon solvents, polar aprotic solvents, ketone solvents or mixtures thereof; suitable temperature ranges from 10 to reflux temperature of the solvent used; isolating in step-d) is by solvent removal by known techniques which are selected from but not limited to distillation, decanting, filtration or cooling the mixture to lower temperatures to precipitate the solid followed by filtration of the mixture.

Further aspect of the present invention provides an improved process for the purification of compound of formula-1 or its pharmaceutically acceptable salts comprising:
a) dissolving compound of formula-1 or its pharmaceutically acceptable salts in a suitable solvent,
b) isolating substantially pure compound of formula-1 or its pharmaceutically acceptable salts.

Wherein suitable solvent in step-a) is selected from polar-aprotic solvents, alcohol solvents, ether solvents, ester solvents, chloro solvents, ketone solvents, polar solvents such as water or mixtures thereof; isolating in step-b) is by solvent removal by known techniques which are selected from but not limited to distillation, decanting, filtration, cooling the mixture to lower temperatures to precipitate the solid followed by filtration of the mixture, crystallization or by adding suitable second solvent which different from the solvent used in step-a), selected from but not limited to alcohol solvents, ester solvents, chloro solvents, nitrile solvents, ketone solvents, polar solvents, water or mixtures thereof.

"Substantially pure" means compound of formula-1 or its pharmaceutically acceptable salts prepared by the process of the present invention is substantially free from the impurities. The compound of formula-1 or formula-1a obtained according to the present invention is substantially pure having a purity >95% by HPLC, preferably >97% by HPLC, more preferably >99% by HPLC.

Preferred embodiment of the present invention provides an improved process for the purification of 4-[3-chloro-4-(N'-cyclopropylureido)phenoxy]-7-methoxyquinoline-6-carboxamide compound of formula-1, comprising:
a) dissolving compound of formula-1 in N-Methylpyrrolidone,
b) combining the solution obtained in step-a) with isopropyl acetate
c) filtering the solid obtained in step-b) to provide substantially pure compound of formula-1.

Further preferred embodiment of the present invention provides an improved process for the purification of 4-[3-chloro-4-(N'-cyclopropylureido)phenoxy]-7-methoxyquinoline-6-carboxamide compound of formula-1 comprising:
a) dissolving compound of formula-1 in dimethyl sulfoxide,
b) combining the solution obtained in step-a) with water,
c) filtering the solid obtained in step-b) to provide substantially pure compound of formula-1.

Figure 10:
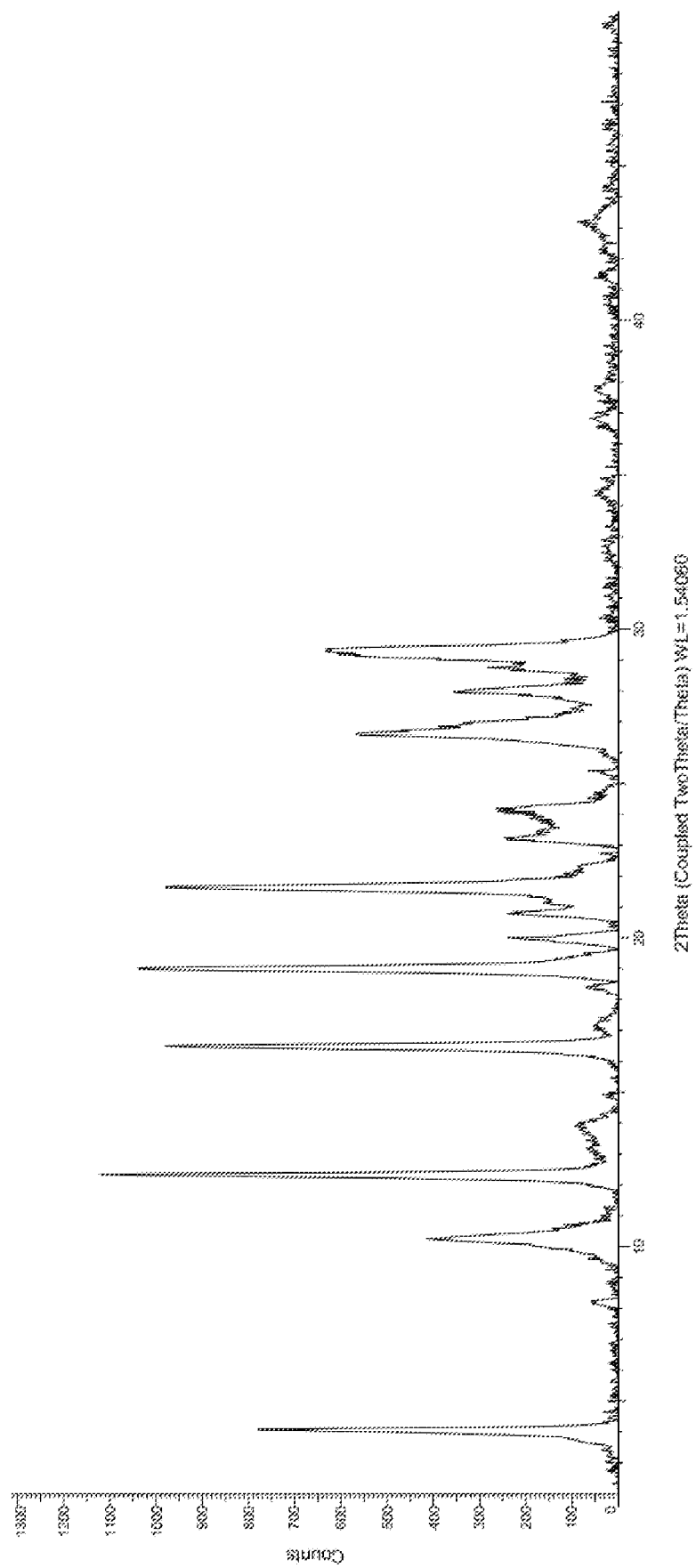
FIG. 10 Illustrates the powder X-Ray diffraction pattern of crystalline form of compound of formula-1 obtained according to Example-20.
Figure 11:
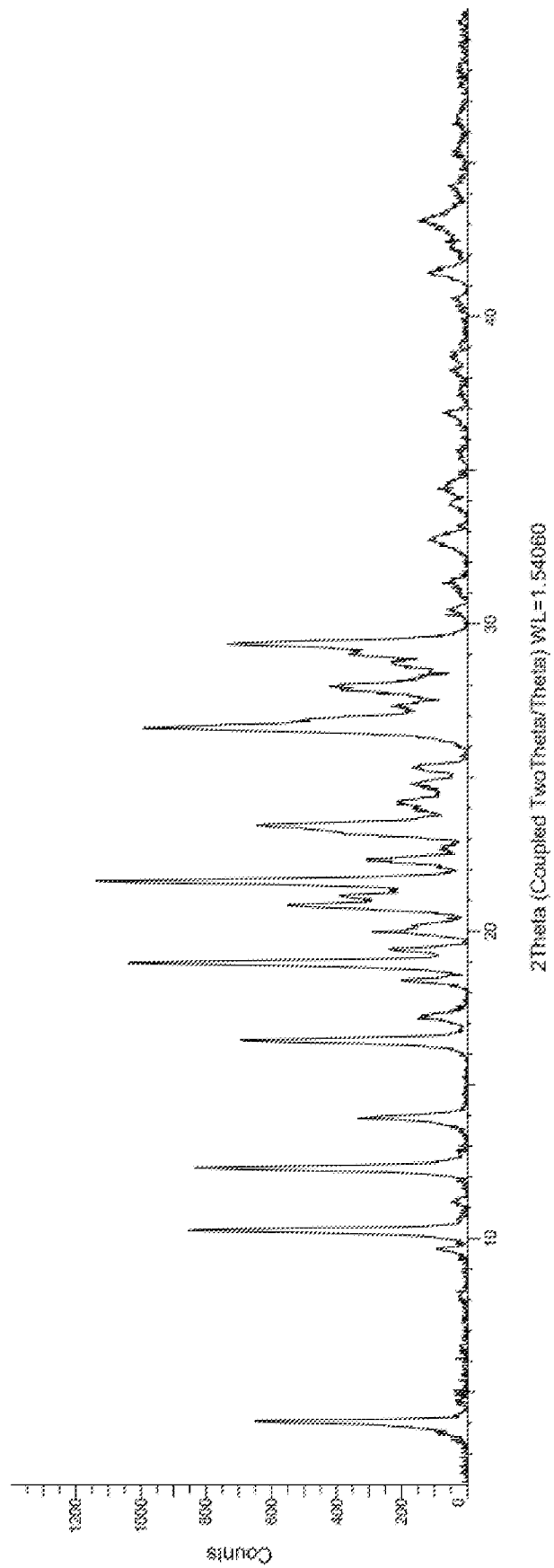
FIG. 11 Illustrates the powder X-Ray diffraction pattern of crystalline form of compound of formula-1 obtained according to Example-21.

4-[3-chloro-4-(N'-cyclopropylureido)phenoxy]-7-methoxyquinoline-6-carboxamide compound of formula-1 obtained according to the present invention is similar to the crystalline form-B of compound of formula-1 described in US20070117842. It is characterized by powder X-Ray diffractogram having peaks at 4.0, 9.6, 10.3, 12.3, 13.9, 16.5, 19.0, 21.6, 26.6, 27.9 and 29.3±0.2 degrees of two-theta and its PXRD pattern is illustrated in FIGS. 10 & 11.

Further aspect of the present invention provides crystalline compound of formula-1 having particle size distribution of D90 is about <200 µm, preferably about <100 µm; D50 is about <100 µm, preferably about <50 µm and D10 is about <30 µm, preferably about <10 µm.

The following impurities are observed during the synthesis of the compound of formula-1 or formula-1a as per the present invention. Along with these impurities, the starting materials are well controlled as per ICH guide lines in the compound of formula-1 or formula-1a.

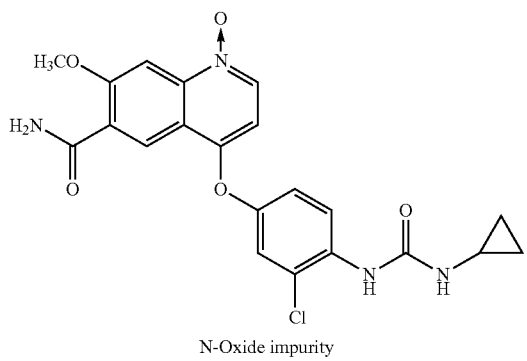

N-Oxide impurity

Descyclopropyl impurity

Dimethyl impurity

N-Ethyl impurity

Cyano carbamate impurity

Hydroxy amide impurity

Cyclopropyl urea impurity

HPLC Method of Analysis:
4-[3-chloro-4-(N'-cyclopropylureido)phenoxy]-7-methoxyquinoline-6-carboxamide or its methane sulfonate and its related substances were analyzed by HPLC with the following chromatographic conditions:

Apparatus: A liquid chromatograph is equipped with variable wavelength UV Detector.
Column: X-Bridge shield RP18, 3.5 µm, 4.6×150 mm (or) Equivalent; Wavelength: 240 nm; Column temperature: 40° C.; Injection volume: 10 µL; Elution: Gradient; Diluent: Acetonitrile: 0.1 OPA; Needle wash: Diluent.
Buffer Preparation:
i) Accurately transfer 1000 ml of milli-Q water into a suitable cleaned and dry beaker.
ii) Weigh accurately 1.36 g of potassium di hydrogen phosphate, 1.74 g of dipotassium hydrogen phosphate and mix well with above 1000 ml of milli-Q-water.
iii) Filter the obtained solution through 0.22 µm PVDF membrane filter paper and sonicate about 3 minutes to degas it.
Mobile phase-A: Buffer 100%; Mobile phase-B: Acetonitrile: Buffer: Methanol.

The PXRD analysis of compound of formula-1 and formula-1a of the present invention was carried out using BRUKER/D8 ADVANCE X-Ray diffractometer using CuKα radiation of wavelength 1.5406 A° and at a continuous scan speed of 0.03°/min.

The compound of formula-1 which is used in the present invention can be prepared by any of the known prior art processes or by the present invention.

The crystalline form-S, form-N, form-N1, form-N2, form-L and form-L1 of compound of formula-1a of the present invention are prepared by the processes as illustrated in the present invention and they are useful for the preparation of various pharmaceutical compositions formulated in a manner suitable for the route of administration to be used where at least a portion of compound of formula-1a is present in the composition in particular polymorphic forms mentioned.

An embodiment of the present invention provides the use of crystalline form-S, form-N, form-N1, form-N2, form-L and form-L1 of compound of formula-a, compound of formula-1 for the preparation of pharmaceutical composition.

The other embodiment of the present invention provides pharmaceutical composition comprising crystalline form-S, form-N, form-N1, form-N2, form-L and form-L1 of compound of formula-1a, compound of formula-1 and at least one pharmaceutically acceptable excipient.

The compound of formula-1 and formula-1a which are used in the present invention can be prepared by any of the known prior art processes.

The crystalline form-S, form-N, form-N1, form-N2, form-L and form-L1 of compound of formula-1a can be utilized as input for the preparation of any of the known polymorphic forms and they can also be used as input for the preparation of other novel crystalline polymorphs of compound of formula-1a.

The crystalline form-S, form-N, form-N1, form-N2, form-L and form-L1 of compound of formula-1a of the present invention are useful and well suitable for the preparation of various pharmaceutical compositions formulated in a manner suitable for the route of administration to be used where at least a portion of compound of formula-1a is present in the composition in particular polymorphic form mentioned. Such pharmaceutical compositions may comprise compound of formula-1a present in the composition in a range of between 0.005% and 100% (wt/wt), with the balance of the pharmaceutical composition comprising additional substances such as excipients, diluents, lubricants, binders, wetting agents, disintegrating agents, glidants, sweetening agents, flavoring agents, emulsifying agents, solubilizing agents, pH buffering agents, perfuming agents, surface stabilizing agents, suspending agents and other conventional pharmaceutically inactive agents.

The crystalline form-S, form-N, form-N1, form-N2, form-L and form-L1 of compound of formula-a of the present invention can be further micronized or milled to get desired particle size to achieve desired solubility profile based on different forms of pharmaceutical composition requirements. Techniques that may be used for particle size reduction includes but not limited to single or multi-stage micronization using cutting mills, pin/cage mills, hammer mills, jet mills, fluidized bed jet mills, ball mills and roller mills. Milling or micronization may be performed before drying or after drying of the product.

The best mode of carrying out the present invention was illustrated by the below mentioned examples. These examples are provides as illustration only and hence should not be construed as limitation of the scope of the invention.

EXAMPLES

Example-1: Preparation of Crystalline Form-S of 4-[3-chloro-4-(N'-cyclopropylureido)phenoxy]-7-methoxyquinoline-6-carboxamide methanesulfonate (Formula-1a)

Dissolved the 4-[3-chloro-4-(N'-cyclopropylureido)phenoxy]-7-methoxyquinoline-6-carboxamide methanesulfonate compound of formula-1a (5 g) in a mixture of dimethylacetamide (150 ml) and water (12.5 ml) at 70 to 75° C. stirred for 10 minutes at the same temperature. The above mixture was slowly added to the pre-cooled methyl isobutyl ketone (300 ml) at 0 to 5° C. and stirred the mixture for 20 minutes at the same temperature. Filtered the precipitated solid and dried to get the title compound.

Yield: 4.1 g. PXRD of the obtained compound as illustrated in FIG. 1 and its DSC thermogram as illustrated in FIG. 2.

Example-2: Preparation of Crystalline Form-N of 4-[3-chloro-4-(N'-cyclopropylureido)phenoxy]-7-methoxyquinoline-6-carboxamide methanesulfonate (Formula-1a)

Dissolved the 4-[3-chloro-4-(N'-cyclopropylureido)phenoxy]-7-methoxyquinoline-6-carboxamide methanesulfonate compound of formula-1a (500 mg) in the mixture of dimethyl sulfoxide (8 ml) and water (2 ml) at 70 to 75° C. and stirred for 10 minutes at the same temperature. The above mixture was slowly added to pre-cooled isobutyl acetate (20 ml) at 0 to 5° C. and stirred the mixture for 30 minutes at the same temperature. Filtered the precipitated solid and dried to get the title compound.

Yield: 350 mg. PXRD pattern of the obtained compound as illustrated in FIG. 3. DMSO Content: 12.2%

Example-3: Preparation of Crystalline Form-N of 4-[3-chloro-4-(N'-cyclopropylureido)phenoxy]-7-methoxyquinoline-6-carboxamide methanesulfonate (Formula-1a)

Dissolved the 4-[3-chloro-4-(N'-cyclopropylureido)phenoxy]-7-methoxyquinoline-6-carboxamide compound of formula-1 (1 g) in dimethyl sulfoxide (10 ml) at 60 to 65° C. and stirred for 10 minutes at the same temperature. Methanesulfonic acid (0.2) followed by isopropanol (20 ml) was slowly added to the above mixture at 60 to 65° C. and stirred for 10 minutes. Slowly cooled the mixture to 10-15° C. and stirred the reaction mixture for 2 hours at the same temperature. Filtered the precipitated solid and dried to get the title compound.

Yield: 800 mg. PXRD pattern of the obtained compound as illustrated in FIG. 4.

Example-4: Preparation of Crystalline Form-N of 4-[3-chloro-4-(N'-cyclopropylureido)phenoxy]-7-methoxyquinoline-6-carboxamide methanesulfonate (Formula-1a)

The mixture of 4-[3-chloro-4-(N'-cyclopropylureido)phenoxy]-7-methoxyquinoline-6-carboxamide compound of formula-1 (5 g) and dimethyl sulfoxide (50 ml) was heated to 40-45° C. and methanesulfonic acid (1.1 ml) was added to the mixture at the same temperature. Further heated the mixture to 65-70° C. and stirred for 10 minutes at the same temperature. Cooled the mixture to 25-30° C. and isobutyl acetate (100 ml) was added to the mixture at the same temperature. Stirred the mixture for 2 hours at 25-30° C. Filtered the precipitated solid and dried to get the title compound.

Yield: 4.2 g. PXRD pattern of the obtained compound is similar to FIG. 4.

Example-5: Preparation of Crystalline Form-N1 of 4-[3-chloro-4-(N'-cyclopropylureido)phenoxy]-7-methoxyquinoline-6-carboxamide methanesulfonate (Formula-1a)

Dissolved the 4-[3-chloro-4-(N'-cyclopropylureido)phenoxy]-7-methoxyquinoline-6-carboxamide methanesulfonate compound of formula-1a (500 mg) in the mixture of dimethyl sulfoxide (8 ml) and water (2 ml) at 80 to 85° C. and stirred for 10 minutes at the same temperature. The above mixture was slowly added to pre-cooled methyl isobutyl ketone (20 ml) at 0 to 5° C. and stirred the mixture at the same temperature for 30 minutes. Filtered the precipitated solid and dried to get the title compound.

Figure 5:
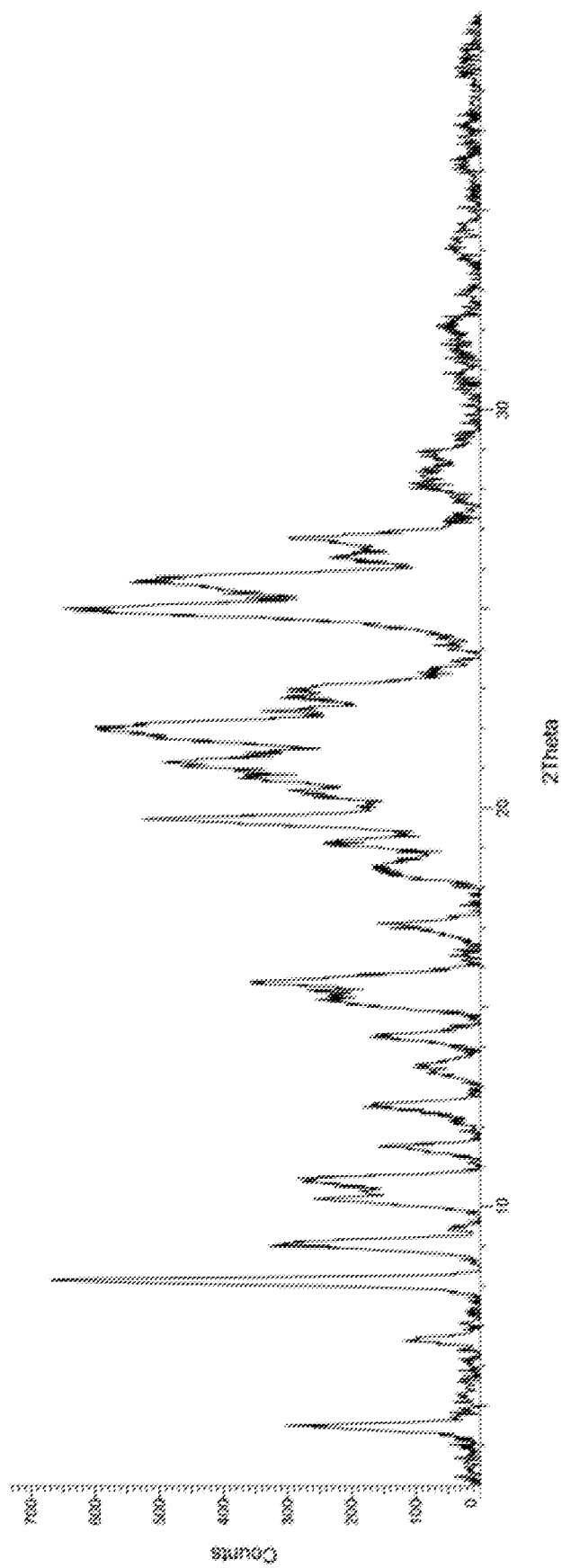

Yield: 400 mg. PXRD pattern of the obtained compound as illustrated in FIG. 5. DMSO Content: 12.6%.

Example-6: Preparation of Crystalline Form-N2 of 4-[3-chloro-4-(N'-cyclopropylureido) phenoxy]-7-methoxyquinoline-6-carboxamide methanesulfonate (Formula-1a)

The mixture of compound of formula-1 (30 g) and dimethyl sulfoxide (300 ml) was stirred for 10 minutes. Methanesulfonic acid (5 ml) was added to the mixture at 25-30 and stirred for 10 minutes at the same temperature. Isobutyl acetate (600 ml) was added to the mixture at the same temperature. Stirred the mixture for 30 minutes at 25-30° C. Filtered the precipitated solid and dried to get the title compound.

Yield: 27 g, DMSO Content: 15%. PXRD of the obtained compound as illustrated in FIG. 6 and its DSC as illustrated in FIG. 7.

Example-7: Preparation of Crystalline Form-N2 of 4-[3-chloro-4-(N'-cyclopropylureido) phenoxy]-7-methoxyquinoline-6-carboxamide methanesulfonate (Formula-1a)

The mixture of 4-[3-chloro-4-(N'-cyclopropylureido)phenoxy]-7-methoxyquinoline-6-carboxamide compound of formula-1 (5 g) dimethyl sulfoxide (50 ml) was heated to 40-45° C. and stirred for 20 minutes at the same temperature. Methanesulfonic acid (0.93 ml) was added to the mixture at 40-45° C. and stirred for 10 minutes at the same temperature. Cooled the mixture to 25-30° C. and isobutyl acetate (50 ml) was added to the mixture at the same temperature. Stirred the mixture for 30 minutes at 25-30° C. Filtered the precipitated solid and dried to get the title compound.

Yield: 3.8 g.

Example-8: Preparation of Crystalline Form-N2 of 4-[3-chloro-4-(N'-cyclopropylureido) phenoxy]-7-methoxyquinoline-6-carboxamide methanesulfonate (Formula-1a)

The mixture of compound of formula-1 (5 g), dimethyl sulfoxide (50 ml) and water (0.17 ml) was heated to 40-45° C. and stirred for 20 minutes at the same temperature. Methanesulfonic acid (0.46 ml) was added to the mixture at 40-45° C. and stirred for 5 minutes at the same temperature. Cooled the mixture to 25-30° C. and isobutyl acetate (100 ml) was added to the mixture at the same temperature. Stirred the mixture for 30 minutes at 25-30° C. Filtered the precipitated solid and dried to get the title compound.

Yield: 4.0 g.

Example-9: Preparation of Crystalline Form-L of 4-[3-chloro-4-(N'-cyclopropylureido)phenoxy]-7-methoxyquinoline-6-carboxamide methanesulfonate (Formula-1a)

Dissolved the compound of formula-1a (500 mg) in mixture of isobutanol (10 ml) and water (5 ml) at 85 to 90° C. and stirred for 10 minutes at the same temperature. The above mixture was slowly added to pre-cooled ethyl acetate (20 ml) at 0 to 5° C. and stirred the mixture at the same temperature for 20 minutes. Filtered the precipitated solid and dried to get the title compound.

Figure 8:
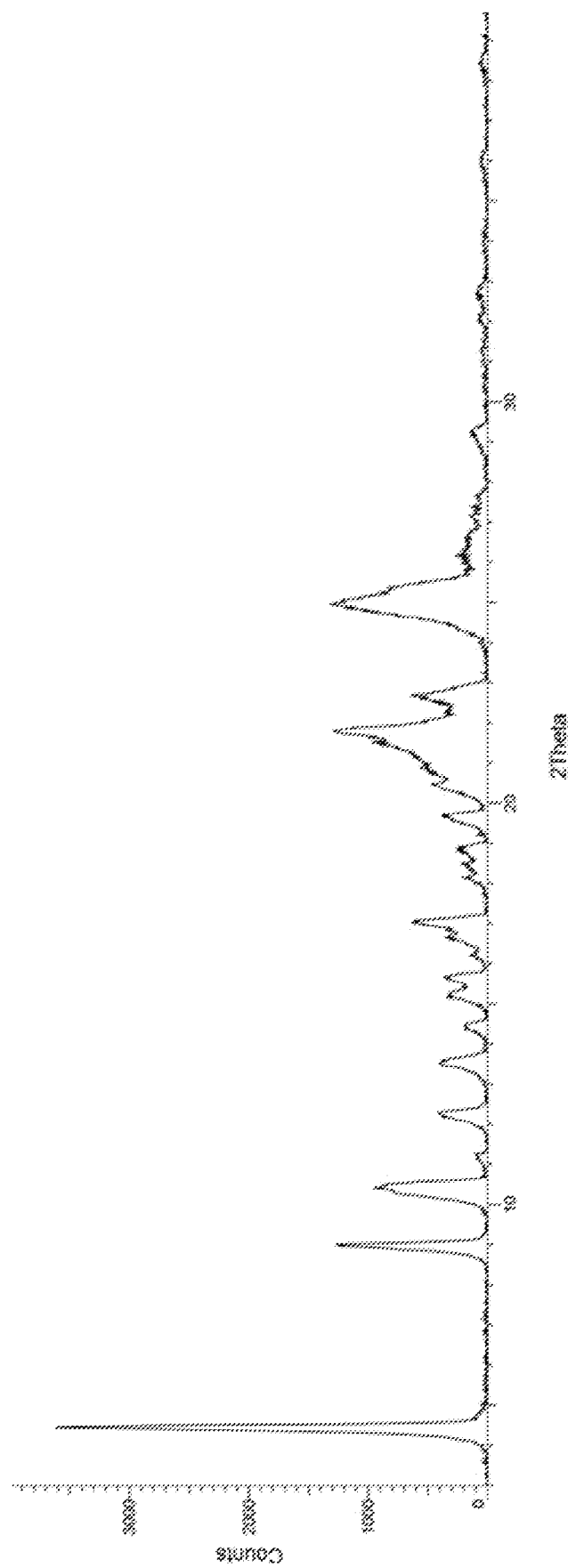

Yield: 300 mg. PXRD pattern of the obtained compound as illustrated in FIG. 8.

Example-10: Preparation of Crystalline Form-L of 4-[3-chloro-4-(N'-cyclopropylureido)phenoxy]-7-methoxyquinoline-6-carboxamide methanesulfonate (Formula-1a)

Dissolved the compound of formula-1a (500 mg) in mixture of isobutanol (10 ml) and water (5 ml) at 85 to 90° C. and stirred for 10 minutes at the same temperature. The above mixture was slowly added to pre-cooled n-butyl alcohol (20 ml) at 0 to 5° C. and stirred the mixture at the same temperature for 20 minutes. Filtered the precipitated solid and dried to get the title compound.

Yield: 400 mg.

Example-11: Preparation of Crystalline Form-L1 of 4-[3-chloro-4-(N'-cyclopropylureido)phenoxy]-7-methoxyquinoline-6-carboxamide methanesulfonate (Formula-1a)

Dissolved the compound of formula-1a (500 mg) in mixture of isobutanol (10 ml) and water (5 ml) at 85 to 90° C. and stirred for 10 minutes at the same temperature. The above mixture was slowly added to pre-cooled methyl isobutyl ketone (20 ml) at 0 to 5° C. and stirred the mixture at the same temperature for 20 minutes. Filtered the precipitated solid and dried to get the title compound.

Yield: 350 mg. PXRD pattern of the obtained compound as illustrated in FIG. 9.

Example-12: Preparation of methyl 4-(((2,2-dimethyl-4,6-dioxo-1,3-dioxan-5-ylidene)methyl)amino)-2-methoxybenzoate[Formula-4a]

24.85 gms of Meldrum's acid compound of formula-2 and 32.71 gms of triethylorthoformate were added to the mixture of methyl 4-amino-2-methoxybenzoate compound of formula-3a (25 gms) and isopropanol (125 ml) at 25-30° C. Heated the reaction mixture to 80 to 85° C. and stirred for 2 hours at the same temperature. The reaction mixture was cooled to 25-30° C. and stirred the reaction mixture for 1 hour at the same temperature. Filtered the precipitated solid, washed with isopropanol and dried to get the title compound.
Yield: 45.7 gm.

Example-13: Preparation of methyl 7-methoxy-4-oxo-1,4-dihydroquinoline-6-carboxylate[Formula-5a]

Heated the mixture of 5 gm of methyl 4-(((2,2-dimethyl-4,6-dioxo-1,3-dioxan-5-ylidene)methyl)amino)-2-methoxybenzoate compound of formula-4a and 65 ml of DOWTHERM A to 185-190° C. and stirred for 15 to 30 minutes at the same temperature. Cooled the reaction mixture to 25-30° C. and stirred the reaction mixture for 1 hour at the same temperature. Filtered the precipitated solid, washed with methyl tertiary butyl ether and dried to get the title compound. Yield: 1.6 gm.

Example-14: Preparation of methyl 4-chloro-7-methoxyquinoline-6-carboxylate [Formula-6a]

27.77 ml of thionyl chloride was added to the mixture of 2 gm of methyl 7-methoxy-4-oxo-1,4-dihydroquinoline-6-carboxylate compound of formula-5a and 0.148 ml of dimethylformamide at 25-30° C. Heated the reaction mixture to 75 to 80° C. and stirred for 2 hours at the same temperature. Cooled the reaction mixture to 45-50° C. and distilled off the reaction mixture under reduced pressure at below 50° C. for removal of excess of thionyl chloride. The reaction mixture was further cooled to 25-30° C. and water followed by dichloromethane were added to the reaction mixture. Separated both the organic and aqueous layers and the aqueous layer was extracted with dichloromethane. Combined the organic layers and washed with aqueous sodium bicarbonate solution. Distilled off the solvent from the organic layer completely under reduced pressure. 6 ml of petroleum ether was added to the obtained compound at 25-30° C. and stirred the mixture for one hour at the same temperature. Filtered the precipitated solid, washed with petroleum ether and dried to get the title compound. Yield: 1.3 gm.

Example-15: Preparation of 4-chloro-7-methoxyquinoline-6-carboxamide [Formula-7]

0.62 ml of formamide was added to the pre-cooled mixture of 0.5 gm of methyl 4-chloro-7-methoxyquinoline-6-carboxylate compound of formula-6a and 2.5 ml of dimethylformamide at 0-5° C. 0.75 gm of sodium methoxide was slowly added to the reaction mixture at 5 to 10° C. and stirred the reaction mixture for 2 hr at same temperature. The reaction mixture was quenched with water at 5 to 10° C. and stirred for 1 hour at the same temperature. Filtered the precipitated solid, washed with water and dried to get the title compound. Yield: 0.1 gm.

Example-16: Preparation of 4-(4-amino-3-chlorophenoxy)-7-methoxyquinoline-6-carboxamide [Formula-8]

4-chloro-7-methoxyquinoline-6-carboxamide (5.05 gms) and dimethyl sulfoxide (45 ml) were added to the mixture of aqueous potassium hydroxide solution and 4-amino-3-chlorophenol hydrochloride (5 gms) at 25-30° C. The reaction mixture was heated to 70-75° C. and stirred for 3 hours at the same temperature. The reaction mixture was cooled to 50 to 55° C. and slowly added 50 ml of aqueous acetone. The reaction mixture was cooled to 5-10° C. and stirred for 1 hour at same temperature. Filtered the precipitated solid and washed with aqueous acetone and dried obtained compound. Further obtained compound was purified by silica gel column chromatography using ethyl acetate and methanol as eluents. Yield: 2.8 gm.

Example-17: Preparation of phenyl (4-((6-carbamoyl-7-methoxyquinolin-4-yl)oxy)-2-chlorophenyl) carbamate [Formula-9a]

0.22 gm of phenyl chloroformate was added to pre-cooled mixture of 4-(4-amino-3-chlorophenoxy)-7-methoxyquinoline-6-carboxamide (1 gm), pyridine (0.5 gm), dimethylformamide (7.5 ml) and water (0.05 ml) at −15 to −20° C. and stirred the reaction mixture for 2 hours at the same temperature. Raised the temperature of the reaction mixture to 5-10° C., tetrahydrofuran was added to the reaction mixture and stirred for 45 minutes at same temperature. Filtered the precipitated solid, washed with tetrahydrofuran and dried to get the title compound. Yield: 0.65 gm.

Example-18: Preparation of 4-[3-chloro-4-(N'-cyclopropylureido)phenoxy]-7-methoxyquinoline-6-carboxamide [Formula-1]

2.46 gm of cyclopropylamine was slowly added to pre-cooled mixture of 5 gm of phenyl (4-((6-carbamoyl-7-methoxyquinolin-4-yl)oxy)-2-chlorophenyl)carbamate and 25 ml of dimethylformamide at 0-5° C. and stirred for 6 hours at the same temperature. Raised the temperature of the reaction mixture to 25-30° C. and stirred for 1 hour at the same temperature. Water and acetone were added to the reaction mixture at 25-30° C. and stirred for 2 hours at the same temperature. Cooled the mixture to 0-5° C. and stirred for 2 hours at same temperature. Filtered the precipitated solid, washed with acetone and dried to get the title compound. Yield: 2 gm.

Example-19: Preparation of 4-[3-chloro-4-(N'-cyclopropylureido)phenoxy]-7-methoxyquinoline-6-carboxamide methanesulfonate [Formula-1a]

0.674 gm methane sulfonic acid was slowly added to the mixture of 2.5 gm of 4-[3-chloro-4-(N'-cyclopropylureido)phenoxy]-7-methoxyquinoline-6-carboxamid and 16.30 ml of acetic acid at 25-30° C. and stirred for 10 minutes. To this mixture, 5 ml of 1-propanol was added and stirred for 10 minutes. Mixture of 17.5 ml of 1-propanol and 12.5 ml of isopropyl acetate were added to the mixture at 25-30° C. and cooled the mixture to 15-20° C. Stirred the mixture for 30 minutes at same temperature. Filtered the precipitated solid, washed with mixture of 1-propanol and isopropyl acetate. Purified the obtained compound using ethanol to get the title compound.

Yield: 1.8 gm.

Example-20: Preparation of 4-[3-chloro-4-(N'-cyclopropylureido)phenoxy]-7-methoxyquinoline-6-carboxamide [Formula-1]

44.3 g of cyclopropylamine was slowly added to pre-cooled mixture of phenyl (4-((6-carbamoyl-7-methoxyquinolin-4-yl)oxy)-2-chlorophenyl)carbamate (180 g) and dimethylformamide (1800 ml) at 0-5° C. and stirred the reaction mixture for 2 hours at the same temperature. Pre-cooled acetone followed by water were added to the reaction mixture at 0-5° C. and stirred for 90 minutes at same temperature. Filtered the precipitated solid, washed with acetone and dried to get the title compound.

Yield: 126 g. PXRD of the obtained compound as illustrated in FIG. 10.

Example-21: Purification of 4-[3-chloro-4-(N'-cyclopropylureido)phenoxy]-7-methoxyquinoline-6-carboxamide [Formula-1]

N-Methyl-2-pyrrolidone (900 ml) was added to 4-[3-chloro-4-(N'-cyclopropylureido) phenoxy]-7-methoxyquinoline-6-carboxamide (126 g) at 25-30° C. and heated the reaction mixture to 65-70° C. and stirred for 10 minutes at the same temperature. Hyflow and carbon were added to the reaction mixture at 60-65° C. and stirred it for 10 minutes. Filtered the reaction mixture through hyflow bed and washed with N-Methyl-2-pyrrolidone. Filtrate was cooled to 25-30° C., isopropyl acetate (2700 ml) was added to it at same temperature and stirred for 2 hours. Filtered the precipitated solid and washed with isopropyl acetate. To the above solid acetone (900 ml) was added at 25-30° C. and stirred for 60 minutes at same temperature. Filtered the solid, washed with acetone and dried to get the title compound.

Yield: 101 g. M.R: 216° C.-222° C. (Decomposition). PXRD of the obtained compound as illustrated in FIG. 11.

Example-22: Preparation of methyl 4-(((2,2-dimethyl-4,6-dioxo-1,3-dioxan-5-ylidene)methyl)amino)-2-methoxybenzoate[Formula-4a]

Heated the mixture triethylorthoformate (306.7 g), methyl 4-amino-2-methoxybenzoate compound of formula-3a (250 g), Meldrum's acid compound of formula-2 (238.64 g) and isopropanol (1750 ml) to 65-70° C. and stirred for 2 hours at the same temperature. The reaction mixture was cooled to 25-30° C. and stirred it for 1 hour at the same temperature. Filtered the precipitated solid, washed with isopropanol and dried to get the title compound.

Yield: 449 g, Purity by HPLC: 99.88%, MR: 194-200° C.

Example-23: Preparation of methyl 7-methoxy-4-oxo-1,4-dihydroquinoline-6-carboxylate[Formula-5a]

Heated the mixture of compound of formula-4a (250 g) and Diphenyl ether (3000 ml) to 185-190° C. and stirred for 2 hours at the same temperature. Cooled the reaction mixture to 30-35° C. and stirred the reaction mixture for 1 hour at the same temperature. Filtered the solid. Acetone was added to above obtained solid at 25-30° C. The mixture was heated to 55-60° C. and stirred for 1 hour at the same temperature. Cooled the mixture to 25-30° C. and stirred for 1 hour at the same temperature. Filtered the solid, washed with acetone and dried to get the title compound.

Yield: 114 g, Purity by HPLC: 97.51%, MR: 238-244° C.

Example-24: Preparation of methyl 4-chloro-7-methoxyquinoline-6-carboxylate [Formula-6a]

The mixture of compound of formula-5a (150 g), dichloromethane (750 ml), dimethylformamide (11.25 ml) and phosphoryl chloride (138 g) was heated to 40-45° C. and stirred it for 7 hours at the same temperature. Cooled the reaction mixture to 25-30° C. and the reaction mixture was quenched into water. Basified the mixture using aqueous potassium carbonate solution at 25-30° C. Both the aqueous and organic layers were separated. Aqueous layer was extracted with dichloromethane. Combined the organic layers and washed with water. Distilled off the solvent completely under reduced pressure and co-distilled with methyl tert-butyl ether. Methyl tert-butyl ether (600 ml) was added to the above obtained solid, mixture was heated to 55-60° C. and stirred for 45 minutes at the same temperature. Cooled the mixture to 25-30° C. and stirred for 1 hour at the same temperature. Filtered the solid, washed with methyl tert-butyl ether and dried to get the title compound.

Yield: 131 g, Purity by HPLC: 99.81%, MR: 136-143° C.

Example-25: Preparation of 4-chloro-7-methoxyquinoline-6-carboxamide [Formula-7]

Formamide (221.74 ml) was added to pre-cooled mixture of compound of formula-6a (200 g) and dimethylformamide (1400 ml) at 0-5° C. Sodium tertiary butoxide (152.72 g) was added in lot-wise to the reaction mixture at 5-10° C. and stirred the reaction mixture for 5 hours at same temperature. The reaction mixture was quenched with pre-cooled water at 5-10° C. and neutralized the mixture with aqueous hydrochloride solution. Heated the mixture to 40-45° C. and stirred the mixture for 1 hours at same temperature. Filtered the solid and washed with water. The obtained compound was recrystallized from the mixture of water and dimethylformamide and dried to get pure title compound.

Yield: 141 g, Purity by HPLC: 99.91%, M.P: 198° C. (Decomposition)

Example-26: Preparation of 4-(4-amino-3-chlorophenoxy)-7-methoxyquinoline-6-carboxamide [Formula-8]

4-chloro-7-methoxyquinoline-6-carboxamide compound of formula-7 (100 g) was added the mixture of 4-amino-3-chloro-phenol hydrochloride (102.7 g), aqueous potassium hydroxide solution (71.13 g of potassium hydroxide in 75 ml of water) and dimethyl sulfoxide (900 ml) at 25-30° C. Heated the reaction mixture to 75-80° C. and stirred for 8 hours at the same temperature. The reaction mixture was cooled to 50-55° C., aqueous acetone was added to reaction mixture and stirred for 10 minutes. The reaction mixture was cooled to 0-5° C. and stirred for 1 hour at same temperature. Filter the precipitated solid, washed with aqueous acetone and dried. N-Methyl-2-pyrrolidone was added to the above obtained solid at 25-30° C. Heated the mixture to 75-80° C. and stirred for 15 minutes at the same temperature. The mixture was cooled to 50-55° C., ethyl acetate was added to the mixture and stirred for 5 minutes. Cool the mixture to 25-30° C. and stirred for 2 hours at same temperature. Filtered the precipitated solid and washed with ethyl acetate. The obtained solid was slurried in acetone, filtered and washed with acetone, dried to get the title compound.

Yield: 101 g, Purity by HPLC: 99.96%, MR: 215-225° C.

Example-27: Preparation of phenyl (4-((6-carbamoyl-7-methoxyquinolin-4-yl)oxy)-2-chlorophenyl) carbamate [Formula-9a]

The mixture of compound of formula-8 (50 g) and dimethylformamide (375 ml) was cooled to −15 to −20° C. Pyridine (46.02 g), sodium bicarbonate (18.32 g) and phenyl chloroformate (56.93 g) were added to the mixture at −15 to −20° C. and stirred the reaction mixture for 1 hour at the same temperature. The reaction mixture was quenched with pre-cooled water. Raised the temperature of the mixture to 20-25° C. and stirred for 1 hour at same temperature. Filtered the solid and washed with water. The obtained solid was slurried in acetone, filter the solid and dried to get the title compound.

Yield: 57 g, Purity by HPLC: 99.66%, MR: 190-198° C. (Decomposition).

Example-28: Purification of 4-[3-chloro-4-(N'-cyclopropylureido)phenoxy]-7-methoxyquinoline-6-carboxamide [Formula-1]

Dissolved compound of formula-1 (150 g) in dimethyl sulfoxide (1050) at 70-75° C. Filtered the solution and washed with dimethyl solfoxide. The obtained filtrate was cooled to 25-30° C., water was added to it at the same temperature and stirred for 1 hour. Filtered the precipitated solid and washed with acetone. The obtained solid was slurried in acetone at 25-30° C. Filtered the solid, washed with acetone and dried to get the title compound.

Figure 12:
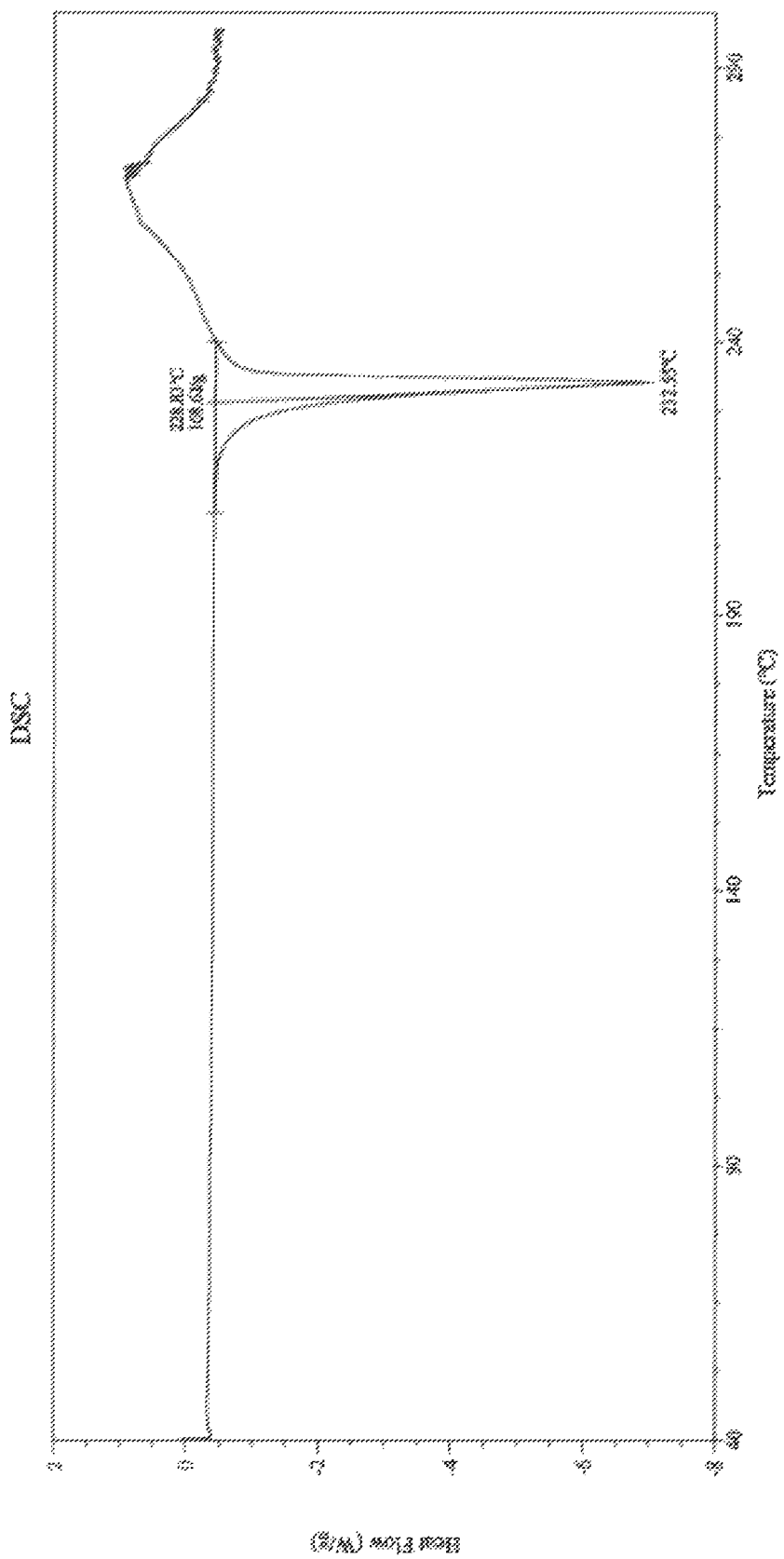
FIG. 12 Illustrates DSC thermogram of compound of formula-1.

Yield: 136 g. Purity by HPLC: 99.89%, N-oxide impurity: Not detected. PXRD of the obtained compound is similar to FIG. 11 and its DSC thermogram as illustrated in FIG. 12. Particle Size distribution of the obtained compound is having D90: 58.7 μm, D50:13.9 μm, D10: 2.6 μm.

Example-29: Preparation of Crystalline Form-N2 of Formula-1a

Methanesulfonic acid (11.7 ml) was added to the mixture of compound of formula-1 (70 g), dimethyl sulfoxide (700 ml) at 25-30° C. and stirred for 10 minutes at the same temperature. Filtered the solution and seeded it with crystalline form-N2 of formula-1a. Stirred the mixture for 1 hour at 25-30° C. Isobutyl acetate (1400 ml) was added to the mixture at 25-30° C. and stirred the mixture for 1 hour at same temperature. Filtered the solid, washed with isobutyl acetate and dried to get the title compound.

Yield: 92 g, Purity by HPLC: 99.84%, N-oxide impurity: Not detected, Descycloprpopyl impurity: 0.01%, Dimethyl impurity: 0.03%, N-ethyl impurity: 0.03%.

PXRD of the obtained compound is similar to FIG. 6 and its DSC thermogram is similar to FIG. 7. Particle Size distribution of the obtained compound is having D90: 92.3 μm, D50: 42.2 μm, D10: 10.6 μm.

We claim:

1. Crystalline form-N2 of 4-[3-chloro-4-(N'-cyclopropylureido)phenoxy]-7-methoxyquinoline-6-carboxamide methanesulfonate of formula-1a:

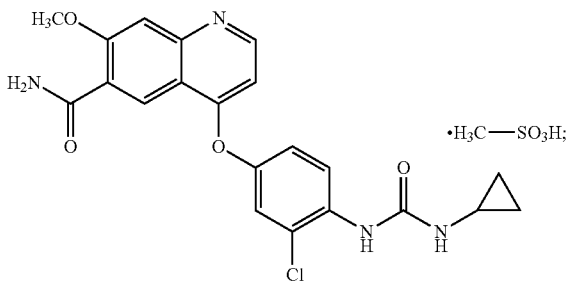

Formula-1a which is characterized by powder X-Ray diffractogram having peaks at about 7.0, 9.0, 13.3, 21.3±0.2° 2θ.

2. The crystalline form-N2 of formula-1a according to claim 1, which is further characterized by powder X-Ray diffractogram having peaks at about 8.9, 12.0, 13.5, 19.2, 21.2, 22.1, 24.2 and 25.7±0.2° 2θ.

3. The crystalline form-N2 of formula-1a according to claim 1, which is characterized by PXRD pattern substantially in accordance with FIG. 6.

4. The crystalline form-N2 of formula-1a according to claim 1, which is characterized by DSC having endotherm peak at about 192±3° C.

5. A process for the preparation of crystalline form-N2 of claim 1, comprising:
   a) providing the solution of compound of formula-1a in a solvent comprising dimethyl sulfoxide, and
   b) isolating the solid to provide crystalline form-N2 of compound of formula-1a.

6. The process according to claim 5, wherein providing the solution of compound of formula-1a in step-a) is by combining compound of formula-1 with methane sulphonic acid in a solvent comprising dimethyl sulfoxide or by dissolving compound of formula-1a in a solvent comprising dimethyl sulfoxide.

7. The process according to claim 5, wherein the solvent in step-a) is selected from the group consisting of alcohol solvents, ester solvents, chloro solvents, nitrile solvents, ketone solvents, polar solvents, water and a mixtures thereof.

8. The process according to claim 5, wherein isolation in step-b) is carried out by removal of the solvent from the mixture by techniques selected from the group consisting of distillation, decanting, filtration, cooling the mixture to lower temperatures to precipitate the solid followed by filtration of the mixture, crystallization or by adding a second solvent which is different from the solvent used in step-a).

9. The process according to claim 8, wherein second solvent is selected from the group consisting of alcohol solvents, ester solvents, chloro solvents, nitrile solvents, ketone solvents, polar solvents, water and a mixture thereof.

10. A process for the preparation of crystalline form-N2 of claim 1, comprising:
   a) adding methane sulfonic acid to the mixture of compound of formula-1 and dimethyl sulfoxide,
   b) optionally adding the seed material of crystalline form-N2 of formula-1a to the solution obtained in step-a),
   c) combining the mixture obtained in step-b) with isobutyl acetate, and
   d) filtering the solid obtained in step-c) to provide crystalline form-N2 of compound of formula-1a.

11. Crystalline form-N2 of formula-1a according to claim 1, which is having particle size distribution of D90 less than 300 μm; D50 less than 100 μm and D10 less than 20 μm.

12. A pharmaceutical composition comprising crystalline form-N2 of 4-[3-chloro-4-(N'-cyclopropylureido)phenoxy]-7-methoxyquinoline-6-carboxamide methanesulfonate of formula-1a of claim 1 and at least one pharmaceutically acceptable excipient.

* * * * *